United States Patent [19]

Shamshoum

[11] Patent Number: 4,864,068

[45] Date of Patent: Sep. 5, 1989

[54] OLIGOMERIZATION PROCESSES AND CATALYSTS

[75] Inventor: Edwar S. Shamshoum, Lake Peekskill, N.Y.

[73] Assignee: UOP, Des Plaines, Ill.

[21] Appl. No.: 271,921

[22] Filed: Nov. 16, 1988

Related U.S. Application Data

[62] Division of Ser. No. 15,704, Jun. 4, 1987.

[51] Int. Cl.$^4$ .................................................. C07C 2/10
[52] U.S. Cl. ................................... 585/514; 585/527; 585/532; 585/533
[58] Field of Search ............... 585/533, 532, 514, 527, 585/528, 529

[56] References Cited

U.S. PATENT DOCUMENTS

| | | | |
|---|---|---|---|
| 4,394,251 | 7/1983 | Miller | 585/533 |
| 4,394,362 | 7/1983 | Miller | 585/533 |
| 4,527,001 | 7/1985 | Kaiser | 585/528 |
| 4,551,236 | 11/1985 | Lok et al. | 585/528 |
| 4,612,406 | 9/1986 | Long et al. | 585/514 |
| 4,788,374 | 11/1988 | Chu et al. | 585/533 |

*Primary Examiner*—Asok Pal
*Attorney, Agent, or Firm*—Vincent J. Vasta, Jr.

[57] ABSTRACT

The invention involves the oligomerization of olefins using a catalyst comprising a composite structure of multiple phases, at least two of which are inorganic crystalline compositions that are contiguous and have a common crystal framework and structure, and at least one of them contains phosphorus and aluminum atoms as part of its crystalline framework structure.

1 Claim, No Drawings

OLIGOMERIZATION PROCESSES AND CATALYSTS

This application is a division of prior U.S. application Ser. No. 15,704, filing date June 4, 1987.

This application is related to copending application Ser. Nos. 058,259, 058,275, and 058,241, commonly assigned and filed on even date herewith.

BRIEF SUMMARY OF THE INVENTION

The invention relates to a process of oligomerizing olefinic compounds by feeding the same through an oligomerization catalyst and to such catalyst which comprises a multi-compositional, multiphase composite comprising different inorganic crystalline compositions, preferably molecular sieve compositions, as phases thereof wherein at least one phase is grown by crystal growth in the presence of another phase, in which:

(a) the different phases are contiguous and have a common crystal framework structure;

(b) one phase contains phosphorus and aluminum atoms as part of the crystal's framework structure, and (c) the composite exhibits distinct compositional heterogeneity of one phase to another therein.

Preferably, the composite comprises a small or intermediate pore non-zeolitic molecular sieve having the same framework structure.

DESCRIPTION OF THE INVENTION

Background to the Invention

Prior Art

There is a phenomenon in heterogeneous catalysis characterized as tortuous diffusion. It involves the passage of gaseous or liquid reactant and reaction product(s) in the porous network of a solid heterogenous catalyst. Tortuous diffusion contemplates contact of the gaseous or liquid reactant and reaction product(s) with the catalytic agent in the porous network of the catalyst for a period longer than the prescribed residence time of the reactants and reaction product(s) in a bed of the catalyst. The length of contact time of the reactants and the reaction product(s) within the catalyst is dependent on the complexity of the porosity and the size of the pores. Catalysts with high surface areas provide a substantial porosity and the reactants or reaction product(s) have a relatively lengthy stay within the catalyst, longer than the calculated residence time. If the reactants and/or the reaction products are capable of generating undesirable products with such passage of time, then a considerable drop in the efficiency of the reaction will occur. One way to avoid the adverse effects of tortuous diffusion is to create a catalyst with low surface area, that is, a solid catalyst which has relatively few pores and a significant number of them are large. However, this cannot be effectively done with all catalysts. Some cannot be effective or exist as a low surface area structure.

There is described herein a novel catalytic oligomerization process which provides a basis for controlling the tortuous diffusion factor as such relates to the oligomerization of olefins with a special class of non-zeolitic molecular sieve catalysts which have immutable crystalline microporous structures.

Copending U.S. patent application Ser. No. 058,259 teaches a new class of molecular sieves based upon the compositing a microporous non-zeolitic molecular sieves (NZMSs) with either another microporous non-zeolitic molecular sieve (NZMS) or a zeolitic molecular sieve (ZMS), or a combination of them. Copending U.S. patent application Ser. No. 058,275 teaches the use of a composite of a NZMS-37, such as SAPO-37 molecular sieve, with another "faujasitic" molecular sieve. Copending U.S. patent application Ser. No. 058,244 teaches the use of a composite of intermediate pore molecular sieves as octane boosting catalysts. These applications provide a detailed discussion of the prior art evolution of microporous non-zeolitic molecular sieves and molecular sieve composite formation as employed to make composites used in this invention; that discussion is incorporated herein by reference.

Included as one of the composites encompassed by the invention of copending U.S. patent application Ser. No. 058,259 are those made to contain small or intermediate pore NZMSs, such as the small or intermediate pore SAPOs, AlPO$_4$s, MeAPOs, MeAPSOs, ELAPOs and ELAPSOs, as described in Table E herein.

Illustrative of such descriptions are those for the SAPO compositional class of small and intermediate pore structure NZMSs set forth in U.S. Pat. No. 4,440,871, patented Apr. 3, 1987. Examples 15–22 characterize the structure of and methods for making SAPO-11, examples 51–53 characterize the structure of and methods for making SAPO-31, examples 46 and 47 characterize the structure of and methods for making SAPO-40, and example 54 characterize the structure of and methods for making SAPO-41. SAPO-11 is there characterized as a crystalline, microporous silicoaluminophosphate having a characteristic X-ray powder diffraction pattern which contains at least the d-spacings set forth in the following Table A:

TABLE A

| 2-Theta | d | Relative Intensity |
|---|---|---|
| 9.4–9.65 | 9.41–9.17 | m |
| 20.3–20.6 | 4.37–4.31 | m |
| 20–2.3 | 4.23–4.17 | vs |
| 21–22.35 | 4.02–3.99 | m |
| 22.5–22.9(doublet) | 3.95–3.92 | m |
| 23.15–23.35 | 3.84–3.81 | m–s |

SAPO-31 is there characterized as a crystalline, microporous silicoaluminophosphate having a characteristic X-ray powder diffraction pattern which contains at least the d-spacings set forth in the following Table B:

TABLE B

| 2-Theta | d | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | W–m |

SAPO-41 is there characterized as a crystalline, microporous silicoalumioophosphate having a characteristic X-ray powder diffraction pattern which contains at least the d-spacings set forth in the following Table C:

TABLE C

| 2-Theta | d | Relative Intensity |
|---|---|---|
| 13.6–13.8 | 6.51–6.42 | w–m |
| 20.5–20.6 | 4 33–4.31 | w–m |
| 21.1–21.3 | 4.21–4.17 | vs |

TABLE C-continued

| 2-Theta | d | Relative Intensity |
|---|---|---|
| 22.1–22.3 | 4.02–3.99 | m-s |
| 22.8–23.0 | 3.90–3.86 | m |
| 23.1–23.4 | 3.82–3.80 | w-m |
| 25.5–25.9 | 3.493–3.44 | w-m |

SAPO-40 is there characterized as a crystalline, microporous silicoaluminophosphate having a characteristic X-ray powder diffraction pattern which contains at least the d-spacings set forth in the following Table D:

TABLE D

| 2-Theta | d | Relative Intensity |
|---|---|---|
| 7.5–7.7 | 11.79–11.48 | VW-M |
| 8.0–8.1 | 11.05–10.94 | S-VS |
| 12.4–12.5 | 7.14–7.08 | W-VS |
| 13.6–13.8 | 6.51–6.42 | M-S |
| 14.0–14.1 | 6.33–6.28 | W-M |
| 27.8–28.0 | 3.209–3.18 | W-M |

The aforementioned specifications and the description in U.S. Pat. No. 4,440,871 provide an appropriate characterization of these intermediate pore structure SAPOs.

The term "small and intermediate pore" refers to the pore size as determined by standard gravimetric adsorption techniques in the art of the referenced crystalline molecular sieve between what is recognized in the art as "large pore" and "small pore," see Flanigen et al, in a paper entitled, "Aluminophosphate Molecular Sieves and the Periodic Table", published in the "New Developments in Zeolite Science and Technology" Proceedings of the 7th International Zeolite Conference, edited by Y. Murakami, A. Iijima and J. W. Ward, pages 103–112 (1986). Intermediate pore crystalline molecular sieves have pores which exist between 0.4 nm and 0.8 nm, especially about 0.6 nm. Such includes for the purposes of this invention crystalline molecular sieves have pores between about 0.5 to about 0.7 nm. Small pore crystalline molecular sieves have pores which exist about 0.4 nm.

Lok et al. Journal of the American Chemical Society, 1984, pp. 6092–6093, describe the intermediate pore SAPOs thusly:

SAPO-11, -31, -40, and -41 are intermediate to large in pore size. Both SAPO-11 and SAPO-41, more readily admit cyclohexane (kinetic diameter, 6.0 Å) than 2,2-dimethylpropane (kinetic diameter, 6.2 Å). SAPO-31 and SAPO-40 adsorb 2,2-dimethylpropane, but exclude the larger triethylamine (kinetic diameter, 7.8 Å). The pore sizes of these structures are defined by either open 10-rings as in silicalite (6 Å) or puckered 12-rings, with 12-rings most probably for SAPO-31 and -40.

New families of crystalline microporous molecular sieve oxides have been recently patented or filed on (by the filing of patent applications), see Table A below, that are based on the presence of aluminum and phosphorus in the framework of the crystal structures. These molecular sieves are actually not zeolites[1] because they are not aluminosilicates and many possess novel crystal structures relative to the known zeolites while others possess framework structures comparable in topology to certain zeolites. For convenience, they are herein characterized as members of the family of "non-zeolitic molecular sieves" which family is generically referred to by the acronym "NZMS". A list of the patents and patent applications covering certain of the NZMSs, and a description of their subject matter, is set out in Table A below. The manufacturing procedures of these new families are employed in the practice of this invention.

[1] According to J. V. Smith, Amer. Mineral Soc. (1963) 1, 281: "a zeolite is an aluminosilicate with a framework structure enclosing cavities occupied by large ions and water molecules, both of which have considerable freedom of movement, permitting ion-exchange and reversible dehydration." See J. Rabo, Zeolite Chemistry and Catalysis, published by the American Chemical Society, Washington, D.C., ASC Monograph 171, 1979, Chapt. 1, p. 3 (J. V. Smith)

Because of the importance of this new family of NZMSs to this invention, it is appropriate to quote from Flanigen et al, in a paper entitled, "Aluminophosphate Molecular Sieves and the Periodic Table", published in the "New Developments in Zeolite Science and Technology" Proceedings of the 7th International Zeolite Conference, edited by Y. Murakami, A. Iijima and J. W. Ward, pages 103–112 (1986), in respect to the nomenclature of those materials:

"The materials are classified into binary (2), ternary (3), quaternary (4), quinary (5), and senary (6) compositions based on the number of elements contained in the catonic framework sites of any given structure. A normalized $TO_2$ formula represents the relative concentration of framework elements in the composition, $(El_xAl_yP_z)O_2$, where El is the incorporated element and x, y and z are the mole fractions of the respective elements in the composition. Acronyms describing the framework composition are shown in Table 1, e.g., SAPO=(Si, Al, P)$O_2$ composition. The structure type is indicated by an integer following the compositional acronym, e.g., SAPO-5 is a (Si, Al, P)$O_2$ composition with the type 5 structure. The numbering of the structure type is arbitrary and bears no relationship to structural numbers used previously in the literature, e.g. ZSM-5, and only identifies structures found in the aluminophosphate-based molecular sieves. The same structure number is used for a common structure type with varying framework composition."

TABLE 1

Acronyms for Framework Compositions

| $TO_2$, T = | Acronym | $TO_2$, T = | Acronym | $TO_2$, T = | Acronym |
|---|---|---|---|---|---|
| Si, Al, P | SAPO | Me, Al, P, Si | MeAPSO | Other Elements: | |
| | | Fe, Al, P, Si | FAPSO | El, Al, P | ElAPO |
| Me, Al, P | MeAPO | Mg, Al, P, Si | MAPSO | El, Al, P, Si | ElAPSO |
| Fe, Al, P | FAPO | Mn, Al, P, Si | MnAPSO | | |
| Mg, Al, P | MAPO | Co, Al, P, Si | CoAPSO | | |
| Mn, Al, P | MnAPO | Zn, Al, P, Si | ZAPSO | | |
| Co, Al, P | CoAPO | | | | |

TABLE 1-continued

| Acronyms for Framework Compositions | | | | | |
|---|---|---|---|---|---|
| TO₂, T = | Acronym | TO₂, T = | Acronym | TO₂, T = | Acronym |
| Zn, Al, P | ZAPO | | | | |

That nomenclature will be followed in characterizing how a particular phase of the composites of this invention are made. For example, if a phase is made by the procedure for making SAPO-11, then the phase will be characterized as a SAPO-11; if a phase is made by the procedure for making SAPO-31, then the phase will be characterized as a SAPO-31; and so on.

It is recognized in the art that the relative acidity of zeolitic molecular sieves can be characterized by their performance in dilute (2 mole %) n-butane cracking, see Rastelli et al., The Canadian Journal of Chemical Engineering, 60, pages 44-49, February 1982. This is true for the NZMS class of molecular sieves. Lok et al., Journal of the American Chemical Society, 1984, 106, 6092-6093. Where reference is made herein to the acidity of a molecular sieve, that acidity characterization is in reference to the material's $k_A$ as determined by its dilute n-butane cracking performance as described by Rastelli et al., supra. In broader terms, acidity means activity in acid catalyzed catalytic reactions generally.

The molecular sieves described in Table E and in the Flanigen et al. article, supra, provide unique catalytic and adsorbent capabilities not as such found in other molecular sieves, particularly the zeolitic molecular sieves. They have a broad range of activity. In most instances, they possess very desirable and superior stability in respect to thermal and hydrothermal properties.

U.S. Pat. No. 4,440,871, one of the patents referred to in Table E, infra, at col. 8, lines 10-16 states the following:

"While not essential to the synthesis of SAPO compositions, it has been found that in general stirring or other moderate agitation of the reaction mixture and/or seeding the reaction mixture with seed crystals of either the SAPO species to be produced or a topologically similar aluminophosphate or aluminosilicate composition, facilitates the crystallization procedure."

Comparable language may be found in many of the other patents and patent applications cited in Table E below, see the notations in this regard in Table E. Specific references are made to examples in the patents and patent applications cited in Table E where seeding was specifically employed. Many of the patents and patent applications of Table E discuss and disclose the use of aluminum and phosphorus containing molecular sieves as a source of aluminum and/or phosphorus in the manufacture of the molecular sieves. None of the patents and patent applications of Table E mention the formation of composites or the formation of multi-compositional, multiphase compositions where the phases are distinct and compositionally heterogeneous as to each other.

SUMMARY OF THE INVENTION

This invention is concerned with the oligomerization of olefins with a catalyst comprising a multi-compositional, multiphase composite that comprise different inorganic microporous crystalline compositions, preferably molecular sieve compositions, as phases thereof wherein at least one phase is grown by crystal growth in the presence of another phase, in which:

(a) the different phases are contiguous and have a common crystal framework structure;

(b) at least one phase contains phosphorus and aluminum atoms as part of the crystal's framework structure, and (c) the composite exhibits a distinct compositional heterogeneity in composition of one phase to another therein.

Preferably, the composite comprises a small or intermediate pore NZMS in combination with another non-zeolitic molecular sieve having the same framework structure.

This invention comprises a process for oligomerizing olefins with a catalyst comprising particulate composition which contains at least 50 weight percent, more preferably at least 75 weight percent, most preferably at least 95 weight percent, and most desirably (and usually) 100 weight percent, of a multi-compositional, multiphase composite comprising different inorganic small or intermediate pore microporous crystalline compositions, preferably molecular sieve compositions, as phases thereof wherein at least one phase is grown by crystal growth in the presence of another phase, in which:

(a) the different phases are contiguous and have a common crystal framework structure;

(b) at least one phase contains phosphorus and aluminum atoms as part of the crystal's framework structure, and (c) the composite exhibits a distinct compositional heterogeneity in composition of one phase to another therein;

and the remainder of the composition comprises, as derived from the composite manufacture, independent particles which are wholly made of a molecular sieve which is of the composition and framework structure of one or more phases of the composite.

This invention, in another aspect, is directed to oligomerizing olefins with a catalyst comprising a multi-compositional, multiphase composite comprising different inorganic microporous crystalline compositions, preferably small or intermediate molecular sieve compositions, as phases thereof wherein at least one phase comprises a deposition substrate upon which another phase is deposited as an outer layer or there are multiple phases jointly formed (such as by differential crystallization), in which:

(a) the different phases are contiguous and have a common crystal framework structure;

(b) at least one phase contains phosphorus and aluminum atoms as part of the crystal's framework structure, and (c) the phase comprising the deposition substrate or one of the phases jointly formed constituting the deposition substrate contains at least about 20 weight percent of the total weight of the phases making up the composite.

DETAILS OF THE INVENTION

This invention is directed to the use of composites as the oligomerization catalyst in which a molecular sieve of the kind characterized in Table E below is in integral lattice association[2] with another structurally compatible inorganic material, inclusive of the molecular sieves of Table E.

[2] It is believed that the integral lattice association (viz. an epitaxial alignment) of the composites of this invention involves a direct chemical linkage between the phases constituting the composite.

The composite catalysts of this invention is an essentially singular microporous crystal structure. Though the composite may be further composited with amorphous or different kinds of crystalline materials, and such is also part of this invention, the microporous crystalline composite is "crystalline" as that term is understood in this art and as further discussed below, and constitutes an unified crystalline structure. The crystalline composite of this invention comprises multiple phases, at least one of which is a NZMS which contains aluminum and phosphorus as part of the crystal framework structure of the phase in question. That means, from a composition standpoint, the unit structure

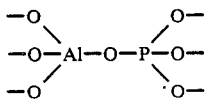

may be present in the crystal framework of the phase.

Another aspect of the invention provides that the various phases of the composite catalysts are integrally bonded to each other by growth of one crystal phase from another such that the crystal structures of the phases yield a composite of a common single crystal structure even though the composite has a heterogeneous chemical composition. The phases are essentially crystallographically indistinct from one another. As pointed out above, the phases of the composites are in integral lattice association with each other. It is believed that the phases are joined together by direct chemical linkages. The phases of the composite catalyst of this invention are not simple blends or physical mixtures that are bonded together by an adhesive generated by a third component which fails to satisfy the crystallographic characterization of the phases and their epitaxial relationships in the composites of this invention. In a most preferred embodiment, the composite catalyst of the invention comprises a core particle enveloped by a shell in which the core and shell constitute different phases contiguously aligned with each other and their crystal framework structures are, in material crystallographic terms, the same.

It has been found that composite catalysts used in the invention containing small and intermediate pore NZMSs can be employed to selectively convert olefin feedstock to oligomer products. The process of the present invention can be used to effect conversion of olefin feeds to dimer, trimer, tetramer, etc., products with high selectivity. The products of such an oligomerization process are primarily olefin oligomers and little or no light cracked products, paraffins, etc. While not wishing to be bound by any theory, it is believed that this desirable result is brought about by a unique combination of appropriate acid strength, crystal structure, and pore size which form products with minimal hydride transfer activity which would tend to form a large fraction of aromatics and that this unique combination helps prevent catalyst deactivation.

The invention thus encompasses the process for the oligomerization of linear and/or branched chain $C_2$ to $C_{12}$ olefins which comprises contacting said olefins at effective process conditions for said oligomerization with an oligomerization catalyst comprising a small or intermediate pore NZMS as a phase of a multiphase composite comprising different inorganic crystalline compositions as phases thereof wherein at least one phase comprises a deposition substrate upon which another phase is deposited or there are multiple phases jointly formed, in which:

(a) the different phases are contiguous and have a common crystal framework structure;

(b) one phase is a small or medium pore NZMS which contains phosphorus and aluminum atoms as part of the crystal's framework structure; and (c) the phase comprising the deposition substrate and one of the phases jointly formed constituting the deposition substrate contains at least about 20 weight percent of the total weight of the phases making up the composite.

The invention also encompasses an oligomerization catalyst comprising a small or intermediate pore NZMS as a phase of a multiphase composite comprising different inorganic crystalline compositions as phases thereof wherein at least one phase comprises a deposition substrate upon which another phase is deposited or there are multiple phases jointly formed, in which:

(a) the different phases are contiguous and have a common crystal framework structure;

(b) one phase is a small or medium pore NZMS which contains phosphorus and aluminum atoms as part of the crystal's framework structure; and (c) the phase comprising the deposition substrate and one of the phases jointly formed constituting the deposition substrate contains at least about 20 weight percent of the total weight of the phases making up the composite.

The preferred NZMS containing composite, as aforedefined, is characterized by an adsorption of triethylamine of less than 5 percent by weight at a pressure of 2.6 torr and a temperature of 22° C.

The composites of the invention as olefin oligomerization catalysts, as aforedefined, allows the oligomerization process to be carried out such that the olefin feed and the NZMS containing composite catalyst are in contact in a liquid phase environment. While not wishing to be bound by any theory, it is believed that by contacting the olefin feed and NZMS catalysts in the liquid phase, i.e., the reactant is supercritical and the products are liquid, one can achieve substantially increased catalyst life, since the liquid phase products tend to "wash" higher boiling products from the surface of the catalyst, thus preventing the build-up of such products and the concomitant blocking of active catalyst sites. When both the reactant olefins and the products are in the vapor phase, higher boiling products tend to deposit on the surface of the NZMS composite catalysts and cause catalyst deactivation by blocking catalytically active sites.

The feedstocks useful in the oligomerization process may be a feedstock containing one or more of the $C_2$–$C_{12}$ olefins, mixtures thereof and/or mixtures of such with $C_1$–$C_5$ paraffins and/or other diluents. Preferred feedstocks include: ethylene, propylene, butenes and mixtures thereof; and a feedstock consisting essentially of $C_2$–$C_5$ linear and/or branched olefins. Further, the feedstock may be an olefin forming feedstock, i.e., a feedstock capable of forming $C_2$–$C_{12}$ linear or branched olefins in situ. The feedstock may, in addition, be any of a number of feeds from other sources including: total gas streams from, for example, a FCC, TCC or Riser cracking unit; a $C_3$ gas fraction from the same or different sources; a $C_4$ mixture from an unsaturated gas plant; the product of a synthesis gas or light alcohol conversion process where such are converted to olefin-containing products; gas streams from a coking unit; and/or may include a partial product recycle of the oligomerization process.

In one embodiment of the instant invention the feedstock from which the $C_2$ to $C_{12}$ olefins are obtained is derived from the conversion of light alcohols and derivative ethers thereof over a ZSM-type zeolite or other methanol to olefins conversion catalyst. Such conversion processes are disclosed in U.S. Pat. Nos. 4,062,905, 4,079,095, 4,079,096, 3,911,041 and 4,049,573, where ZSM-type zeolites are employed as catalysts. The designation "ZSM-type" is meant to refer to those zeolites generally identified in the prior art as "ZSM-n" where "n" is an integer. Further processes for converting methanol and dimethyl ether to olefin products are disclosed in European Application No. 6,501 (catalyst is HZSM-5); European Application No. 2,492 (catalyst is Mn exchanged 13X zeolite); German Offen. No. 2,909,928 (catalyst is Fe exchanged "Silicalite"); Angew. Chem. Int. Ed., 19,2(1980), 126-7 (catalyst is Mn exchanged chabazite and erionite); South African 78/2527 (catalyst is CaH-Fu-1 zeolite); and European Application No. 11,900 (catalyst is boron modified silica).

As mentioned above, olefin-containing feedstocks derived from the conversion of methanol, i.e., light alcohols and derivative ethers thereof, may be advantageously employed in the instant process as the feedstock for the oligomerization of $C_2$ to $C_{12}$ olefins. In such an integrated process the conversion of light alcohols to olefins may be carried out in a first stage or it may be carried out concurrently with the oligomerization process, i.e., the methanol conversion catalyst and the NZMS composite catalyst may be placed in the same reaction zone such that olefin oligomerization occurs as olefin is formed. In general, such a two-step process provides for the production of hydrocarbon products containing greater than five carbons and comprises:

(a) converting a light alcohol and/or derivative ethers thereof to olefin products at effective conversion conditions over a conversion catalyst, preferably a ZSM-type catalyst; and (b) oligomerizing said olefin products of step (a) at effective process conditions by contacting said olefin products with a NZMS composite catalyst.

The conversion conditions employed in the instant process, such as temperature, pressure, space velocity and molar ratio of co-fed diluent to olefin reactants will affect the process and the products formed thereby. In general the process is carried out at effective process conditions, i.e., conversion conditions such that oligomerization of said starting olefin occurs, preferably such that at least 20 percent by weight of the starting olefin is oligomerized to products containing a higher carbon number than the starting olefin(s), more preferably at least 70 percent by weight. Optimum conversion conditions are those in which motor fuel products are the major products, e.g. high octane gasoline component products (boiling between about 80° F. and about 420° F.) and/or diesel oil products (boiling between about 300° F. and about 700° F.) are obtained and hence considerations of temperature and pressure will be selected within a range of conversion levels designed to provide the highest selectivity to and maximum yield of such products.

The process of this invention is conducted such that conversion of the olefin feedstock may be carried out in either the liquid-phase or the vapor-phase.) by contacting the NZMS composite and $C_2$ to $C_{12}$ olefin in a reaction zone, such as, for example, a fixed bed of catalyst, under effective conversion conditions, said catalyst composition being characterized, as synthesized, as comprising one or more of the defined NZMS composite compositions. This process may be conducted in either fixed or fluid bed operation with the attendant benefits of either operation readily obtainable.

The effective conversion conditions employed in carrying out the olefin oligomerization include an effective temperature(s), pressure(s), weight hourly space velocity, contact time(s) and, if employed, an effective amount of diluent. The process is generally carried out at an effective temperature between about 200° F. and 1000° F., preferably between about 300° F. and about 600° F., and at effective pressures ranging between about atmospheric up to about 150 atmospheres or higher, although subatmospheric pressures may be employed. The pressure is preferably between about one atmosphere (0 psig.) and about 100 atmospheres. The weight hourly space velocity (WHSV) of the $C_2$–$C_{12}$ olefin is generally maintained at between about 0.01 $hr^{-1}$ and about 25 $hr^{-1}$ and is preferably between about 0.1 $hr^{-1}$ and about 1.0 $hr^{-1}$.

In most cases it is preferred to employ a diluent in the process, including, but not limited to: $C_1$–$C_4$ paraffins (methane, ethane, propane, isobutane and n-butane); inert gases, such as nitrogen, carbon dioxide; water (and/or steam); and hydrogen. The preferred diluents are paraffinic homologs of the reactant olefins and water.

The effective amount of diluent which may be present in the instant process is not narrowly critical, although specific effective amounts of some diluents may exist, e.g., water. The amount of diluents may vary within the range of from 0 to about 99 weight percent, more preferably between about 1 and about 95 weight percent, based on the weight of total feedstock, i.e., diluent and $C_2$–$C_{12}$ olefins. The amount of diluent is more preferably within the range between about 10 and about 70 weight percent. The NZMS composite catalysts, as above defined for use herein, are generally benefited by co-fed water which has been observed to aid in resisting coking and aging of the NZMS composite containing catalyst under vapor phase conditions, although such effect may not be the only advantage provided by use of water as a diluent.

The effective contact time employed for the oligomerization may vary from seconds to hours and is generally between about 0.05 and about 4 hours and is preferably between about 0.1 and about 2 hours.

Crystalline molecular sieves, whether zeolites or of the NZMS variety, are formed as small crystals ranging in size from about 0.1 microns ($0.4 \times 10^{-5}$ inch) to about 75 microns (0.003 inch) in average cross-sectional area, usually between 0.1–10 microns. The spread in particle size for any particular molecular sieve is about 10 microns in average cross-sectional area. Crystalline molecular sieves are not spheres, they can range from regularly to irregularly shaped structures in the fashion of most crystals. Many are formed as part of agglomerations of crystals.

It is well known in the art to make molecular sieves by incorporating into a gel of the components for growing the molecular sieve crystals a seeding compound having a crystal structure common to that which is being produced. Typically, the amount of seed ranges up to 10 wt. % of the inorganic oxide component of the molecular sieve, see, e.g., examples 51 and 53 of U.S. Pat. No. 4,440,871. In such instances, one finds the following:

. The seed is not characterized as a distinctive feature of the structure.

. The characterizations of the compositions made by the seeding technique fail to note any property contribution of the seed crystals.

The seeding technique is typically noted for facilitating crystal formation.

It is assumed that the seed crystals are so overwhelmed by the concentration of the gel that the ultimate molecular sieve is unaffected property-wise by utilization of the seed. The seeded compositions are not believed to possess many of the useful (and in some cases, unique) properties of the composites of this invention.

In addition, a number of references speak about the use of aluminophosphates, either as crystalline or amorphous structures, as suitable sources of phosphorus or aluminum in making aluminum and phosphorus containing molecular sieves. In view of the fact that the resulting composition is a homogeneous structure in which the digestion of the aluminophosphate reagent appears to be sufficiently complete, it is assumed that none is present either to act as a seed or to impact on the properties of the generated molecular sieve. This recognition that aluminophosphates which have the capacity of seeding can be dissolved in the gel so that they become a source for aluminum and phosphorus for creating a molecular sieve of a NZMS type demonstrates that much of the seeding can be accomplished by little of the seed because so much of the seed can be dissolved to supply reagents for the composition of the NZMS. It is not established that the benefits of seeding depend upon the retention of the particulate shape of the seed. Such disclosures of seeding and using aluminophosphate as a reagent can be found in the patents recited in Table E below.

Seeding adds cost to the manufacture of molecular sieves. Though seeding reduces the induction period in crystal nucleation, which is a cost saving, the cost of making the seed, which manufacture involves a similar nucleation induction period, significantly outweighs that advantage. Consequently, seeding is typically a laboratory tool to facilitate the manufacture of certain molecular sieves. Because seeding adds cost to the manufacture of molecular sieves, the seed typically represents a small part of the ultimate solids content of the molecular sieve. The term "solids content" of a molecular sieve represents the inorganic oxide which remains after the calcination of the precursor to the calcined sieve. Seeding effects nucleation in the gel stage of the manufacture. How nucleation works is not thoroughly understood. However, because seeding operates with a small amount of seed, and because some amount of the seed's surface is dissolved by the gel medium, the ultimate portion of the seed in the seeded particle can be significantly less than the indicated portion of seed used for seeding. The seed contributes processing advantages, not product advantages.

It is significant to note that the use of a molecular sieve as a seed by the prior art for the generation of another molecular sieve yields a product which is not characterized as distinguishable from a molecular sieve of the same composition, but which is made without such a seed.

It has been determined that much of the benefits of NZMSs as catalysts or absorbents are achieved in the outer surface portion (mantle) of the sieve particle. Where a NZMS is employed as a catalyst in a chemical reaction in which irreversible secondary reactions occur that generate by-products, much of the primary reaction occurs in the outer mantle and much of the secondary reaction(s) occurs in the core area of the molecular sieve particle. This phenomena is believed to be, to a large extent, the product of the tortuous diffusion of the adsorbate(s) through the core of the molecular sieve particle which increases the adsorbate(s)'s contact with the catalyst. This extra contact with an active catalyst phase results in undesired secondary reaction(s) being promoted.

The efficiency or selectivity of a chemical reaction is measured by the ability of the catalyst to generate the primary reaction product(s) while avoiding or minimizing the formation of the irreversible (in the context of the reactions) secondary reaction product(s). In this context, it should be appreciated that a secondary reaction product is considered an undesired by-product of the reaction. This invention is directed to providing NZMS catalysts that achieve enhanced efficiencies or selectivities to the primary reaction product(s) while minimizing the adverse secondary reactions.

This invention provides for an absorbent particulate composite composition suitable as an oligomerization catalyst that possesses a differentiation in catalytic activity and/or selectivity within the particle at different parts thereof. This is accomplished through selection of the composition of the phases of the composite and the nature of their placement in the composite's structure. If the core of the composite is made of a phase that is less active than the layer or phase surrounding it, then the reaction product of a tortuous diffusion of reactant to the core will result in less secondary reaction products being formed than if the whole particle were made of the composition of the surrounding layer. Higher selectivities are the result.

This invention is directed to the use of a sufficient amount of a phase within a multi-compositional, multi-phase catalyst composite that the compositional heterogeneity of the various phases are maintained. When utilizing one phase as a deposition substrate for another phase, the deposition substrate must be present in the ultimate composite in such an amount that it retains its identity as a distinct phase within the composite, that is, the composite is clearly composed of phases which are compositionally heterogeneous with each other but are topologically compatible with each other. This is regarded, in characterizing this invention, as providing that a deposition substrate constitute at least about 20 wt. % of the total weight of the phases making up the composite. In other words, the language "of at least about 20 wt. %" is intended to mean that the amount of the deposition substrate phase present in the composite is sufficient for it to have a separate and distinct heterogeneous compositional identity vis-a-vis the other phases of the composite.

The nature of the deposition of one phase upon the other in the composite is believed to be that of a layer of a phase directly upon the surface of another phase. In such a representation, the deposited layer is termed herein the "outer layer" and the substrate phase providing the deposition surface is termed the "deposition substrate." This terminology holds even though more than two phases exist in the composite.

The invention also encompasses an oligomerization catalyst comprising a heterogeneous mixture comprising:

(A) a multi-compositional, multiphase composite comprising different inorganic crystalline molecular sieve compositions as phases thereof wherein at least one phase is grown by crystal growth in the presence of another phase, in which:

(a) the different phases are contiguously aligned to each other and possess a common crystal framework structure;

(b) at least one phase contains phosphorus and aluminum atoms as part of the crystal's framework structure;

(c) the composite exhibits a distinct compositional heterogeneity of one phase to another therein; and (B) an inorganic crystalline composition which is not so contiguously aligned and not sharing a common crystal framework structure with the multi-compositional, multiphase composite of (A), but is bonded to the multi-compositional, multiphase composite of (A), or (C) an amorphous composition which is bonded to the multi-compositional, multiphase composite of (A).

The invention includes the utilization of a multi-compositional, multiphase microporous molecular sieve oligomerization catalyst structure wherein at least one of the phases comprises a molecular sieve embraced by an empirical chemical composition on an anhydrous basis expressed by the formula:

(e) $mR:(Q_wAl_xP_ySi_z)O_2$     (I)

where "Q" represents at least one element present as a framework oxide unit "$QO_2^n$" with charge "n" where "n" may be $-3$, $-2$, $-1$, $0$ or $+1$; "R" represents at least one organic templating agent present on the intracrystalline pore system; "m" represents the molar amount of "R" present per mole of $(Q_wAl_xP_ySi_z)$ and has a value from zero to about 0.3; and "w", "x", "y" and "z" represent the mole fraction of $QO_2^n$, $AlO_2^-$, $PO_2^+$, $SiO_2$, respectively, present as framework oxide units. "Q" is characterized as an element having a mean "T-O" distance in tetrahedral oxide structures between about 1.51 Å and about 2.06 Å. "Q" has a cation electronegativity between about 125 kcal/g-atom to about 310 kcal/gm-atom and "Q" is capable of forming stable Q-O-P, Q-O-Al or Q-O-Q bonds in crystalline three dimensional oxide structures having a "Q-O" bond dissociation energy greater than about 59 kcal/g-atom at 298° K[3]; and said mole fractions being within the limiting compositional values or points as follows:

w is equal to 0 to 98 mole percent;
y is equal to 1 to 99 mole percent;
x is equal to 1 to 99 mole percent; and
z is equal to 0 to 98 mole percent.

[3] See the discussion at pages 8a, 8b and 8c of EPC Application 0 59 624, infra, about the characterization of "EL" and "M". Such are equivalent to Q as used herein.

The "Q" of the "QAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. The invention contemplates combinations of the elements as representing Q, and to the extent such combinations are present in the structure of a QAPSO they may be present in molar fractions of the Q component in the range of 1 to 99 percent thereof. It should be noted that formula (I) contemplates the non-existance of Q and Si. In such case, the operative structure is that of $AlPO_4$ as discussed above. Where z has a positive value, then the operative structure is that of SAPO, discussed above. Thus, the term QAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various compositions and structures described in the patents and patent applications set forth in Table A, which follows, and by Flanigen et al., in the paper entitled Aluminophosphate Molecular Sieves and the Periodic Table, supra:

TABLE E

| Patent or Pat. Applic. No. | Subject Matter of Patent or Patent Application |
|---|---|
| U.S. Pat. No. 4,567,029 | MeAPO's are crystalline metal aluminophosphates having a three-dimensional microporous framework structure of $MO_2^{-2}$, $AlO_2^-$ and $PO_2^+$ tetrahedral units and having an empirical chemical composition on an anhydrous basis expressed by the formula $mR:(M_xAl_yP_z)O_2$; where R represents at least one organic templating agent present in the intracrystalline pore system; m has a typical value of from 0 to 0.3 and represents the moles of R present per mole of $(M_xAl_yP_z)O_2$; M represents magnesium, manganese, zinc or cobalt, x, y and z represent the mole fractions of M, aluminum and phosphorus, respectively, present as tetrahedral oxides. The fractions are such that they are within a tetragonal compositional area defined by points ABC and D of FIG. 1 of the drawings of the patent. This patent, at column 6, describes the use of aluminophosphates as a source of phosphorus (lines 26–28) and as a source of aluminum (lines 38–40), and the use of seed crystals to aid in the crystallization of the desired molecular sieve (lines 59–63). Example 85 depicts the use of MAPO-36 as a seed for making MnAPO-36. The chemical composition of the MnAPO-36 fails to reveal the presence of any magnesium. |
| U.S. Pat. No. 4,440,871 | SAPO molecular sieves are a general class of microporous crystalline silicoaluminumophosphates. The pores have a nominal diameter of greater than about 3Å. The "essentially empirical composition" is $mR:(Si_xAl_yP_z)O_2$, where R represents at least one organic templating agent present in the intracrystalline pore system; m has a typical value of from 0 to 0.3 and represents the moles of R present per mole of $(Si_xAl_yP_z)O_2$; x, y and z represent the mole fractions of silicon, aluminum and phosphorus, respectively, present as tetrahedral oxides. The fractions are such that they are within a pentagonal compositional area defined by points A, B, C, D and E of the ternary diagram of FIG. 1 and preferably within the pentagonal compositional area defined by points a,b,c,d and e of FIG. 2, of the drawings of the patent. The SAPO molecular sieves have a characteristic x-ray powder diffraction pattern which contains at least the d-spacings set forth in any one of Tables I, III, V, VII, IX, XI, XIII, XV, XVII, XIX, XXIII or XXV of the patent. Further, the as-synthesized crystalline silicoaluminophosphates of the patent may be calcined at a temperature sufficiently high to remove at least some of any organic templating agent present in the intracrystalline pore system as a result of such synthesis. The silicoaluminophosphates are generally referred to therein as "SAPO", as a class, or as "SAPO-n" wherein "n" is an integer denoting a particular SAPO as its preparation is reported in the patent. The U.S. patent speaks at column 8, lines 12–16 of employing seed crystals to generate SAPO species. That technique is described in examples 21, 51 and 53. |
| U.S. Ser. No. 600,312 filed April 13, 1984, commonly assigned, EPC Publication 0 159 624, published Oct. 30, 1985 | ELAPSO molecular sieves have the units $ELO_2^n$, $AlO_2^-$, $PO_2^+$, $SiO_2$ in the framework structure and have an empirical chemical composition on an anhydrous basis expressed by the formula: $mR:(EL_wAl_xP_ySi_z)O_2$ where "EL" represents at least one element present as a framework oxide unit "$ELO_2^n$" with charge "n" where "n" may be −3, −2, −1, 0 or +1; "R" represents at least one organic templating agent present on the intracrystalline pore system; "m" represents the molar amount of "R" present per mole of $(EL_wAl_xP_ySi_z)O_2$ and has a value from zero to about 0.3; and "w", "x", "y" and "z" represents the mole fractions of $ELO_2^n$, $AlO_2$, $PO_2^+$, $SiO_2$, respectively, present as framework oxide units. "EL" is characterized as an element having (a) a mean "T–O" distance in tetrahedral oxide structures between about 1.51 Å and about 2.06 Å, (b) a cation electronegatively between about 125 kcal/g-atom to about 310 kcal/gm-atom and (c) a capability of forming stable M—O—P, M—O—Al or M—O—N bonds in crystalline three dimensional oxide structures having a "m—O" bond dissociation energy greater than about 59 kcal/g-atom at 298° K. "w", "x", "y" and "z" represent the mole fractions of "EL", aluminum, phosphorus and silicon, respectively, present as framework oxides. The "EL" represents at least one element capable of forming a framework tetrahedral oxide and is preferably selected from the group consisting of arsenic, beryllium, boron, chromium, cobalt, gallium, germanium, iron, lithium, magnesium, manganese, titanium and zinc and "w", "x", "y" and "z" represent the mole fractions of "EL", aluminum, phosphorus and silicon, respectively, present as tetrahedral oxides. The EP publication at page 16 discloses the use of crystalline and amorphous aluminophosphate as a source of phorphorus and aluminum and at page 17 describes seeding the reaction mixture. Examples 11A, 12A, 93A-103A, 5B, 6B, 55B, 58B, 59B, 50D-56D, 59D-62D and 12F-15F depict the use of seed crystals. |
| U.S. Pat. No. 4,500,651, patented Feb. 19, 1985 | TAPO molecular sieves comprise three-dimensional microporous crystalline framework structures of $[TiO_2]$, $[AlO_2]$ and $[PO_2]$ tetrahedral units which have a unit empirical formula on an anhydrous basis of: $mR:(Ti_xAl_yP_z)O_2$ wherein "R" represents at least one organic templating agent present in the intracrystalline pore system; "m" represents the moles of "R" present per mole of $(Ti_xAl_yP_z)O_2$ and has a value of from zero to 5.0, the maximum value in each case depending upon the molecular dimensions of the templating agent and the available void volume of the pore system of the particular titanium molecular sieve; "x", "y" and "z" represent the mole fractions of titanium, aluminum and phosphorus, respectively, present as tetrahedral oxides. The TAPO molecular sieves are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The U.S. patent at column 8, lines 65–68, and column 9, lines 15–18, discusses the use of crystalline amorphous aluminophosphate as a source of phosphorus and aluminum. At column 6, lines 1–5, seeding is described as facilitating the crystallization procedure. Comparative example 44 describes a composition of amorphous $TiO_2$ and 95 wt. % $AlPO_4$-18 without an indication of how the composition was prepared. |
| U.S. Ser. No. 600,179, filed Apr. 13, 1984, EPC Publication 0 161 488, published Nov. 21, 1985. | The TiAPSO molecular sieves have three-dimensional microporous framework structures of $TiO_2$, $AlO_2^{2-}$, $PO_2^+$ 600,179, filed having an empirical chemical composition on an anhydrous basis expressed by the formula: $mR:(Ti_wAl_xP_ySi_z)O_2$ wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined in respect to the |

TABLE E-continued

| Patent or Pat. Applic. No. | Subject Matter of Patent or Patent Application |
|---|---|
| U.S. Pat. No. 4,554,143, patented Nov. 19, 1985 | ternary diagram of FIG. 1 of the applications.<br>The publication, at page 13, describes the use of crystalline or amorphous aluminophosphate as a source of phosphorus and aluminum and, at page 14, points out that seeding the reaction mixture facilitates the crystallization procedure.<br>Ferroaluminophosphates (FAPO's) are disclosed in U.S. Pat. No. 4,554,143; incorporated herein by reference, and have a three-dimensional microporous crystal framework structure of $AlO_2$, $FeO_2$ and $PO_2$ tetrahedral units and have an essential empirical chemical composition, on an anhydrous basis, of:<br>$mR:(Fe_xAl_yP_z)O_2$<br>wherein "R" represents at least one organic templating agent present in the intracrystalline pore system; "m" represents the moles of "R" present per mole of $(Fe_xAl_yP_z)O_2$ and has a value of from zero to 0.3; the maximum value in each case depending upon the molecular dimensions of the templating agent and the available void volume of the pore system of the particular ferroaluminophosphate involved; "x", "y" and "z" represent the mole fractions of iron, aluminum and phosphorus, respectively, present as tetrahedral oxides. When synthesized the minimum value of "m" in the formula above is 0.02.<br>The iron of the $FeO_2$ structural units can be in either the ferric or ferrous valence state, depending largely upon the source of the iron in the synthesis gel. Thus a $FeO_2$ tetrahedron in the structure can have a net charge of either −1 or −2.<br>The patent indicates at column 5, lines 43–45 and 54–56, that crystalline amorphous aluminophosphate may be used as a source of phosphorus and aluminum and at column 6, lines 1–5, describes seeding of the reaction mixture as facilitating the crystallization procedure. |
| U.S. Application Ser. No. 600,173, filed April 13, 1984, EPC Publication 0 161 491, published Nov. 21, 1985 | The FeAPSO molecular sieves have a three-dimensional microporous crystal framework structures of $FeO_2^{-2}$ (and/or $FeO_2$), $AlO_2$, $PO_2$ and $SiO_2$ tetrahedral oxide units and having a unit empirical formula, on an anhydrous basis, of:<br>$mR:(Fe_wAl_xP_ySi_z)O_2$ (1)<br>wherein "R" represents at least one organic templating agent present in the intracrystalline pore system; "m" represents the moles of "R" present per mole of $(Fe_wAl_xP_ySi_z)O_2$ and has a value of from zero to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides. |
| U.S. Ser. No. 600,170, EPC Publication 0 158 975, published Oct. 23, 1985 | The EP publication, at page 12, describes the use of seeding the reaction mixture to facilitate the crystallization procedure. At page 18, the publication describes the use of crystalline amorphous aluminophosphates as a source of phosphorus and aluminum in making the molecular sieve.<br>The ZnAPSO molecular sieves of U.S. Ser. No. 600,170, filed April 13, 1984 comprise framework structures of $ZnO_2^{-2}$, $AlO_2^-$, $PO_2^+$ and $SiO_2$ tetrahedral units having an empirical chemical composition on an anhydrous basis expressed by the formula:<br>$mR:(Zn_wAl_xP_ySi_z)O_2$<br>wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01.<br>This publication at page 13 discloses that crystalline or amorphous aluminophosphate may be used as a source of phosphorus or aluminum and at page 14 indicates that seeding of the reaction mixture with said crystals facilitates the crystallization procedure. Examples 12–15 are stated to employ the seeding procedure. |
| U.S. application Ser. No. 600,180, filed April 13, 1984, EPC Publication 0 158 348, published Oct. 16, 1985 | The MgAPSO molecular sieves have three-dimensional microporous framework structures of $MgO_2^{-2}$, $AlO_2^-$, $PO_2^+$ and $SiO_2$ tetrahedral oxide units and have an empirical chemical composition on an anhydrous basis expressed by the formula:<br>$mR:(Mg_wAl_xP_ySi_z)O_2$<br>wherein "R" represents at least one organic templating agent present in the intracrystalline pore system; "m" represents the molar amount of "R" present per mole of $(Mg_wAl_xP_ySi_z)O_2$ and has a value from zero to about 0.3; and "w", "x", "y" and "z" represent the mole fractions of magnesium, aluminum, phosphorus and silicon, respectively, present as tetrahedral oxides and each preferably has a value of at least 0.01. This publication depicts seeding to generate product at page 14 and in examples 5, 6, 55, 58 and 59. |
| U.S. Application Ser. No. 600,175, filed April 4, 1984 EPC Publication 0 161 490 published Nov. 11, 1985 | The MnAPSO molecular sieves of U.S. Ser. No. 600,175, filed April 13, 1984 have a framework structure of $MnO_2^2$, $AlO_2$, $PO_2$ and $SiO_2$ tetrahedral units having an empirical chemical composition on an anhydrous basis expressed by the formula:<br>$mR:(Mn_wAl_xP_ySi_z)O_2$<br>wherein "R" represents at least one organic templating agent in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides.<br>The publication at page 13 describes the use of crystal or amorphous aluminophosphate as a source of phosphorus or aluminum, and at page 14 characterizes the use of said crystals to facilitate the crystallization procedure. Examples 54–56 and 59–62 state such crystals were used in the manufacture of the MnAPSO products. |
| U.S. Application Ser. No. 600,174, filed April 13, 1984 EPC Publication 0161 489 published Nov. 21, 1985 | The CoAPSO molecular sieves of U.S. Ser. No. 600,174, filed April 13, 1984 have three-dimensional microporous framework structures of $CoO_2^2$, $AlO_2$, $PO_2$ and $SiO_2$ tetrahydral units and have an empirical chemical composition on an anhydrous basis expressed by the formula:<br>$MR:(Co_wAl_xP_ySi_z)O_2$<br>wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represents the mole fractions of cobalt, aluminum, phosphorus and silicon, respectively, present as tetrahedral oxides, where the mole fractions "w", "x", "y" and "z" are each at least 0.01. |

4,864,068

TABLE E-continued

| Patent or Pat. Applic. No. | Subject Matter of Patent or Patent Application |
|---|---|
| U.S. Pat. applications 599,771 599,776 599,807, 599,809, 599,811 599,812 599,813 600,166 600,171 each filed April 13, 1984 EPC Publication 0 158 976 published Oct. 23, 1985 | The EP publication at page 13 depicts the use of crystalline amorphous aluminophosphate as a source of phosphorous and aluminum and at page 14 states that seeding the reaction mixture facilitates the crystallization procedure. Examples 11, 12, 13, 93, and 97-103 depict the use of seed crystals. MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,028. Members of this novel class of compositions have a three-dimensional microporous crystal framwork structure of $MO_2^{-2}$, $AlO_2^-$ and $PO_2^+$ tetrahedral units and have the essentially empirical chemical composition, on an anhydrous basis, of: $mR:(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y" and "z" represent the mole fractions of the metal "M", (i.e., magnesium, manganese, zinc and cobalt), aluminum and phosphorus, respectively, present as tetrahedral oxides. When synthetized the minimum value of "m" in the formula above is 0.02. The as-synthesized compositions are capable of withstanding 350° C. calcination in air for extended periods, i.e., at least 2 hours, without becoming amorphous. The EP publication at pages 14 and 15 depicts the use of crystalline and amorphous aluminophosphate as a source of phosphorus and aluminum and at page 15 states that seeding the reaction mixture facilitates the crystallization procedure. Example 8 discloses seeding of crystals. |
| EPC Applic. 85104386.9, filed April 11, 1985 (EPC Publication No. 015896, published October 13, 1985) and EPC Applic. 85104388.5, filed April 11, 1985 (EPC Publication No. 158348 published October 16, 1985) | "ELAPO" molecular sieves are in a class of crystalline molecular sieves in which at lest one element capable of forming a three-dimensional microporous framework form crystal framework structures of $AlO_2$, $PO_2$ and $MO_2$ tetrahydral oxide units wherein "$MO_2$" represents at least one different element (other than Al or P) present as tetrahedral oxide units "$MO_2$" with charge "n" where "n" may be $-3$, $-2$, $-1$, 0 or $+1$. The numbers of this novel class or molecular sieve compositions have crystal framework structures of $AlO_2$, $PO_2$ and $MO_2$ tetrahedral units and have an empirical chemical composition on an anhydrous basis expressed by the formula: $mR:(M_xAl_yP_z)O_2$ wherein "R" represents at least one organic templating agent present in the intracrystalline pore system; "m" represents the molar amount of "R" present per mole of $(M_xAl_yP_z)O_2$; "M" represents at least one element capable of forming framwork tetrahedral oxides; and "x", "y" and "z" represent the mole fraction of "M", aluminum and phosphorous, respectively, present as tetrahedral oxides. "M" is at least one different elements (M1) such that the molecular sieves contain at least one framework tetrahedral units in addition to $AlO_2$ and $PO_2$. "M" is at least one element selected from the group consisting of arsenic, beryllium, boron, chromium, gallium, germanium and lithium, and when "M" denotes two elements, the second element may be one of the aforementioned and/or is at least one element selected from the group consisting of cobalt, iron, magnesium, titanium and zinc. The ELAPO molecular sieves are generally referred to herein by the acronym or "ELAPO" to designate element(s) "M" in a framework of $AlO_2$, $PO_2$ and $MO_2$ tetrahedral oxide units. Actual class members will be identified by replacing the "EL" of the acronym with the elements present as $MO_2$ tetrahydral units. When "M" denotes two elements "M" may also be at least one element selected form the group consisting of cobalt, iron, magnesium, manganese, titanium and zinc. For example, in each instance "M" includes at least one of the first group of elements, e.g., As, Be, etc, and when two or more elements are present, the second and further elements may be selected from the first group of elements and/or the second group of elements, as above discussed. The ELAPO molecular sieves have crystalline three-dimensional microporous framework structures of $AlO_2$, $PO_2$ and $MO_2$ tetrahedral units and have an empirical chemical composition on an anhydrous basis expressed by the formula: $mR:(M_xAl_yP_z)O_2$; wherein "M" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc. The relative amounts of element(s) "M", aluminum and phosphorus are expressed by the empirical chemical formula (anhydrous): $mR:(M_xAl_yP_z)O_2$ where "x", "y" and "z" represent the mole fractions of said "M", aluminum and phosphorus. The individual mole fractions of each "M" (of when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x" hereinafter, where "$x_1$" + "$x_2$" + "$x_3$" ... = "x" and where $x_1$, $x_2$, $x_3$, etc. are each at least 0.01. The ELAPO molecular sieves have crystalline three-dimensional microporous framework structures of $MO_2$, $AlO_2$ and $PO_2$ tetrahedral units having an empirical chemical composition of an anhydrous basis expressed by the formula: $mR:(M_xAl_yP_z)O_2$ wherein "m" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides. $AlPO_4$ are the basic and simplet of the crystalline aluminophosphate based molecular sieves. They each having a framework structure whose chemical composition expressed in terms of mole ratios of oxides is: $Al_2O_3:1.0 \pm 0.2P_2O_5$; |
| U.S. Pat. No. 4,310,440 | each of said framework structures being microporous in which the pores are uniform and have nominal diameters within the range of about 3 to about 10 Å, an intracrystalline |

TABLE E-continued

| Patent or Pat. Applic. No. | Subject Matter of Patent or Patent Application |
|---|---|
| U.S. Pat. Applications 600,168 600,181, 600,182, 600,183, European Patent Publ. 0 158 350, published Oct. 16, 1985 | adsorption capacity for water at 4.6 torr and 24° C. of at least 3.5 weight percent, the adsorption and desorption of water being completely reversible while retaining the same essential framework topology in both the hydrated and dehydrated state.<br>SENAPSO are quinary and senary molecular sieves that have framework structures of at least two elements having tetrahedral oxide units "$MO_2{}^n$" and having $AlO_2{}^-$, $PO_2{}^+$ $SiO_2$ tetrahedral oxide units, where "n" is $-3$, $-2$, $-1$, 0 or $+1$, and have an empirical chemical composition on an anhydrous basis expressed by the formula:<br>$mR:(M_wAl_xP_ySi_z)O_2$<br>wherein "R" represents at least one organic templating agent present in the intracrystalline pore system; "m" represents the molar amount of "R" present per mole of $(M_wAl_xP_ySi_z)O_2$ and has a value of from 0 to about 0.3; "M" represents at least two elements selected from the group consisting of arsenic, beryllium, boron, chromium, cobalt, gallium, germanium, represent the mole fractions of elements "M", aluminum, phosphorus and silicon, respectively, present as tetrahedral oxides, each having a value of at least 0.01<br>The publication, at pages 14–15, generally describes seeding reaction mixtures to form the desired product. |

Of the multiple phases of the compositions of this invention, at least one of them contains aluminum and phosphorus in the framework structure. At least one of the phases, in a preferred embodiment of this invention, contains the QAPSO structure of formula (I) above. The remaining compositions of the other phase(s) may be a different QAPSO embraced by formula (I) or another crystalline molecular sieve structure of either the zeolitic or non-zeolitic variety. Typical of the molecular sieves of the zeolitic varieties are those classed as intermediate or small pore zeolites, and others, such as chabazite, levynite, Linde Type A, gismondine, erionite, analcime, gmelinite, harmotome, mordenite, epistilbite, heulandite, stilbite, edingtonite, mesolite, natrolite, scolecite, thomsonite, brewsterite, laumontite, phillipsite, the ZSM's (e.g., ZSM-5[4], ZSM-20[5], ZSM-12[6], ZSM-34[7], etc.) and Beta [8], and the like. Specifically, certain zeolite molecular sieves can be employed as a composite phase, preferably as a deposition substrate, in the oligomerization catalysts. For example, NZMS-17 structures can be composited with erionite, NZMS-34 structures with chabazite, NZMS-35 structures with levynite, NZMS-42 structures with type A zeolites, NZMS-43 structures with gismondine, and the NZMS-44 structures and -47 structures with chabazite-like zeolites.

[4] See U.S. Pat. No. 3,702,886.
[5] See U.S. Pat. No. 3,972,983.
[6] See U.S. Pat. No. 3,832,449.
[7] See U.S. Pat. No. 4,086,186.
[8] See U.S. Pat. No. 3,308,069 and U.S. Pat. No. Re. 28,341.

In characterizing the various phases of the composites, reference is being made to specific chemical compositions which are already known in the art because the phases (viz. SAPO-11) that are made start with either such a chemical composition already made or utilize a method of manufacture which according to the art would generate such a known chemical composition. This does not mean that the chemical composition of the phases is the full equivalent to such characterization. It is believed that whether one starts with an already formed known composition or produces a phase by a procedure which is intended to generate a known composition, that in significant ways the resulting phases in the composite of this invention are different in chemical composition from either the composition initially started with or the intended composition that the procedure was designed to generate. This difference in chemical composition is not reflected in a change in the crystal structure. The significant difference resides in the chemical composition of the interface(s) of the phases. The capacity exists for significant ionic mobility of extra framework cations during the manufacturing of molecular sieves. This generates a significant amount of ion transfer by ion exchange to occur. Where one composition is deposited upon another of a different kind, there is a greater propensity for such ion exchange to occur. Moreover, during the deposition of one phase onto another, there is a propensity for redissolving a part of the deposition substrate by the components of the outer layer causing a chemical change to that portion of the interface which nominally belongs to the deposition substrate. Frequently, this change at the interface constitutes a chemicals redistribution between the components of the outer layer being deposited and the deposition substrate which is redissolved. Because one is dealing in atomic layers, the degree of compositional alteration is quite small and does not constitute a gross alteration of the composition of any particular phase. Consequently, there is not seen in the composition enough changes in the chemical composition of a phase such that by nuclear magnetic resonance ("NMR") one can detect a dramatic compositional change in the framework sites of any of the phases. Even though such a change occurs, the crystal structure is predictable and accords with the known crystal structure of the deposition substrate and that which is expected for the outer layer. However, one cannot state with certainty the exact chemical composition of each of the phases of the composites of the catalysts of this invention.

For example, a SAPO-11 phase in composites of this invention is not believed to be completely identical to the SAPO-11 made in accordance with Examples 16-22 of U.S. Pat. No. 4,440,871 where those compositions meet at an interface with another molecular sieve composition, in a composite embodied by this invention.

The crystal structure of the composites, or any phase thereof, is determined in accordance with standard analytical procedures of the art. Though the art frequently relies upon X-ray powder diffraction analysis to define or differentiate a molecular sieve from the prior art, it should be appreciated that the characterization of the crystal structure is not solely dependent upon that type of analysis. There are instances where X-ray powder diffraction analysis will not generate a suitable pattern in order to properly characterize the presence of a crystal structure. Such does not mean that the structure is not crystalline. Other procedures can be employed to demonstrate the existence of a crystal structure. The characterization of a crystal structure is typically determined according to a number of analytical techniques, one of which is X-ray powder diffraction analysis. Such techniques include, by way of example, electron diffraction analysis, molecular adsorption data, and adsorption isotherm characterizations. Some phases used in the composites of this invention may not show a distinctive X-ray powder diffraction pattern adequate for crystal structure characterization. The other techniques in combination allow one to determine the nature of the crystal lattice in which the phase exists. There are cases where the crystal structure is even ill-defined by a combination of techniques, but according to the evidence arrayed, such is characterizable as crystalline by comparison with a particular structure. Such a pseudo-crystalline structure is deemed a crystal for the purpose and understanding of this invention.

The phases of the composites used in the invention relate to each other because they each possess essentially the same crystalline framework structure. In practical terms, this means that the X-ray powder diffraction patterns for the composite (or other evidence of crystallinity) of the multiple phases is the same in essential details other than those affected by changes in the size of different framework cations. Though it is possible for each of the phases to have different X-ray diffraction patterns, the differences should be slight enough that in essential crystallographic terms one would regard the different structures to be framework compatible. This is intended to mean that the various phases have crystalline structures which mimic each other in terms of framework topology.

It is important to recognize that the significant advantage of the composites used in this invention over the single compositions which correspond to the proposed composition of a phase of a composite or blends of such single compositions corresponding to the phases of the composite, resides in the superior performance one may achieve from the use of the composite as an oligomerization catalyst relative to the single compositions or the blends of such compositions.

Even so, a particularly desirable embodiment of this invention involves the use of a relatively inexpensive crystalline molecular sieve for one phase, and a high performance and more costly QAPSO molecular sieve for another phase. It has been determined that the composite exhibits the properties of the costlier component or properties which are superior to those of the costlier component, in each case at a much reduced cost. In some cases, the composite provides substantially better performance on a given QAPSO weight basis than such QAPSO alone. Indeed, such better performance is seen when comparing a given weight of the composite against the most superior performing of the molecular sieves used in making the composite, even over a cost reduced basis. Because the composite is superior to the individual QAPSO in most respects, and is superior to the less costly molecular sieve component in almost all respects, the composite yields a synergistic benefit totally unexpected and unique in the field of catalysis.

Another determination arising from this invention, is a recognition that NZMSs which are more active to an oligomerization reaction than another NZMS or a zeolitic molecular sieve, will operate in respect to that chemical or chemical reaction almost as if the other NZMS or the zeolitic molecular sieve were inactive relative to such chemical or chemical reaction, provided they are composited as herein contemplated. As a result, an active synthetic zeolitic molecular sieve can be composited about a more active NZMS without adversely affecting the activity of the NZMS in respect to the adsorbate or the chemical reaction. In such case, care has to be taken to avoid caustic attack of the NZMS. Viewing such composites as cores surrounded by layers, characterized as one or more mantle layers surrounding the core, then such active zeolitic molecular sieve should occupy a relatively thin mantle layer surrounding the NZMS. If the zeolite mantle layer were too thick, then the porous labyrinth of the zeolite could become so extensive that the adsorbate or the chemical reaction has minimum access to the NZMS layer or core, as the case may be. Such would diminish the ability of the more active NZMS from fully affecting the chemical or the chemical reaction. As a result, it is possible to add a mantle of a relatively inexpensive molecular sieve about another mantle made from a more expensive and more active and/or selective NZMS for the purpose of protecting the NZMS from decomposition or fracturing without adversely affecting the overall benefits derived from the activity and/or selectivity of the NZMS.

If one practices the invention with a view to cost reduction in the production of extremely effective non-zeolitic molecular sieves, then it is desired to produce composites in which the phases thereof containing the NZMS are present in the minimum acceptable amounts. It has been determined, quite surprisingly, that the performance characteristics at least equivalent to a wholly NZMS can be achieved in the composite structures of this invention by utilizing substantially less of the NZMS and substituting in the composition for the NZMS materials the topographically functional equivalent zeolitic molecular sieve (ZMS) material. It has been determined that if the composite contains at least a phase made of a NZMS and at least a phase made of a ZMS, that the ZMS constitute the predominant amount by weight of the phases making up the composite because the advantages in adsorbent and catalyst properties of the NZMSs can be essentially achieved with a material reduction in cost.

The benefits of this invention are achieved when the outer layer constitutes less than 80 weight percent of the composite. In most instances, it will be desirable to have the outer layer constitute less than about 60 weight percent, more preferably less than about 50 weight percent, of the weight of the composite. It has been found in most, if not essentially all cases, less secondary reactions occur when the outer layer comprises a smaller weight or volume of the composite molecular sieve. When the outer layer constitutes more than 80 weight percent of the composite, the composite tends to behave as if it were 100 weight percent the composition and structure of the outer layer, and secondary reaction generation is more pronounced when such are used as catalysts as herein characterized. This trend in secondary reactions tends to drop as the weight of the outer layer diminishes.

In the another aspect of this invention, one may employ composites in which the amount of the deposition substrate therein range from at least about 20 weight percent of the total weight of the composite up to about 98 weight percent of the total weight of the composite and the amount of the outer layer phase or phases ranges from about 80 weight percent of the total weight of the composite down to about 2 weight percent of the total weight of the composite. In a preferred aspect of this invention, one may employ composites in which the amount of the deposition substrate therein range from at least about 40 weight percent of the total weight of the composite up to about 98 weight percent of the total weight of the composite and the amount of the outer layer phase or phases ranges from about 60 weight percent of the total weight of the composite down to about 2 weight percent of the total weight of the composite. In a more preferred case, the composite will be made of two phases and the amount of the deposition substrate in the composite will range from about 50 to about 95 weight percent of the total weight of the composite and the outer layer will constitute from about 5 to 50 weight of the composite.

In the typical case, the outer layer (mantle) has a thickness which is less than that of the deposition substrate layer. In the typical case, the outer layer will weigh less than the deposition substrate. The reason for this, in the typical case, is the fact that one will generally choose to employ an aluminum and phosphorus containing phase as the outer layer. In a practical application of this invention, it will be desirable to combine a relatively inexpensive zeolitic molecular sieve with the more costly aluminum and phosphorus containing molecular sieve. Such zeolitic molecular sieves are produced in large volumes, therefore it will be desirable to employ a commercial presynthesized zeolite in making the composite. It follows that such will be a logical choice for the deposition substrate. Those facts coupled with the desire to use the minimum amount of the more costly and better performing aluminum and phosphorus containing phase typically results in employing a smaller weight amount of the outer layer relative to the weight of the deposition substrate. In such a case, it will be desirable that the outer layer contain from about 2 to about 50, preferably about 2 to about 40, weight percent of the total weight of the composite, and the remaining weight be that of the less costly molecular sieve, such as a zeolitic molecular sieve, or a less active NZMS such as an AlPO$_4$.

In a preferred embodiment of this invention, the composite is a small particle in the range of from about 0.2 to about 10 microns in average cross-section. The preferred embodiment of the particle comprises an internal core area circumscribed by one or more mantles. If there are more than one mantle, one is an outer layer relative to the other and to the core. For the purpose of describing this invention, as set forth in this specification and the claims, an inner mantle which circumscribes a core, and optionally another and more internal mantle, is termed a core relative to a mantle external of it. Each mantle in contact with each other is made of a different chemical composition and each mantle and core in contact are made of different chemical compositions. The particle need not be spherical for the purposes of the invention in order to have the aforementioned core/mantle relationship. The core may be an aggregate of particles about which resides a mantle layer. The particles are typically polyhedral in shape. They may contain dendrites and/or spherulites. The ultimate particle may be part of an agglomerate of the particles.

These benefits of the invention can be appreciated by recognizing that microporous molecular sieves have pores which extend throughout the crystal structure. Most of the catalyst's surface area is found in these pores. It is the pore surface area which provides essentially all of the catalyst's active sites. As the feedstock enters the interior of the catalyst, it progresses a labyrinthian or tortuous course, as such or as reaction products generated in the catalyst. Tortuous diffusion dictates that given enough contact time, some of the primary reaction products will react with active sites on the catalyst's pore surface and such generally results in the formation of lower molecular weight products. By reducing the size of the labyrinthian course provided by the most active catalyst species the problems associated with tortuous diffusion are reduced. As a result, the selectivity to primary product is enhanced because the level of contact time within the most active portion of the catalyst is controlled sufficiently to minimize the generation of secondary reaction(s).

A special advantage of the composite structures of this invention resides in the fact that the depth of the layer of a given phase of the composite provides a mechanism for controlling the performance characteristics of that phase as a catalyst. If the phase is extremely active owing to a too high level of acidity, one may retain a high level of catalytic activity while minimizing the destructive features (e.g. secondary reactions) of the high acidity. It is known that the destructive aspects of an acidic and hence active catalyst is dependent upon the residence time a reactant spends in the catalyst. By depositing a small layer of the active phase onto a deposition surface which is relatively inert to the reactant (vis-a-vis the outer layer), the contact time of the reactant with the catalyst, in particular the outer layer, is minimized to the extent that the destructive feature of the catalyst is minimized. It is axiomatic that a useful catalyst which has a propensity to destroy primary reaction products and generate unwanted by-products, does so at a rate lower than the desired catalyzed reaction, otherwise the catalyst would yield little in benefits. By reducing the thickeners of the active catalyst layer, the tortuous diffusion contact time will also be reduced in the active catalyst. This should improve the selectivity of the catalyst to produce the desired reaction products and minimize secondary reaction products. The layered composite catalysts of this invention provide such a benefit by controlling the depth of the outer layer, and hence the tortuous diffusion, to accomodate the activity of the outer layer to the desired reaction and reaction products.

Thus, a factor in the design of a composite catalyst made according to this invention is the consideration of the various reactions which may be affected by the catalyst. If the reaction simply involves a conversion of

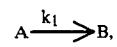

then little criticality with respect to selectivity over the amount and size of the outer layer is seen. However, if the reaction generates irreversible by-products ("C") as in the case of

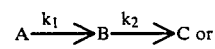

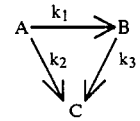

where the secondary reactions $k_2$ and $k_3$ generate undesired by-products C, then it is preferred that the contact within the catalyst be sufficiently limited to the depth of the outer, more active layer such that the predominant reaction is $k_1$ and reactions $k_2$ and/or $k_3$ are minimized, if not avoided. In this way, the catalytic impact is more selective in the case of these layered catalysts than in the full catalyst particle where the outer layer composition is the whole of the particle composition.

The composites of this invention can be made by the hydrothermal crystallization of reactive gel precursors to the crystal structure in the presence of a support surface for crystal growth thereon. The gel precursors depend upon the structure being made. In the case of an aluminosilicate based crystal framework, the precursors are the typical aluminate and silicate compositions employed for making such aluminosilicates. Indeed, a characteristic of this invention is that each phase may be made by conventional procedures in the art for making the composition of the particular phase. It is generally not necessary to employ a new process for generating a phase in the presence of another phase in order to enjoy the fruits of this invention.

In the case of composites to be made using a zeolitic molecular sieve recipe calling for the use of extremely high pHs, e.g., operating at pH's of 12 or higher, typically more in a pH range of 13-14, such as caused by the use of caustic reagents as sodium hydroxide, it may be necessary that such recipes be used for the manufacture of the deposition substrate and not an outer substrate. Such recipes may cause the decomposition of the deposition substrate and thus the fundamental integrity of the composite when they are used in forming the outer layer. It is desirable to operate at a lower pH using ammonium salts to at least substitute for some of the caustic in the recipe when making outer layers of zeolitic molecular sieve.

The class of non-zeolitic aluminum and phosphorus based molecular sieves are typically synthesized by hydrothermal crystallization of reactive aluminum and phosphorus containing gels containing optionally the additional framework elements and an organic template, at temperatures from about 50° C. (122° F.) to about 250° C. (482° F.), preferably from about 100° C. (212° F.) to about 225° C. (437° F.). The optimum crystallization temperature depends on composition and structure. The AlPO₄ and SAPO materials tend not to crystallize at temperatures below about 125° C. (257° F.), whereas several of the MeAPO species crystallize readily at about 100° C. (212° F.).

QAPSO compositions are generally synthesized by hydrothermal crystallization from a reaction mixture containing active sources of element(s) "Q" (optional), silicon (optional), aluminum and phosphorus, preferably an organic templating, i.e., structure-directing, agent which is preferably a compound of an element of Group VA of the Periodic Table, and optionally, an alkali or other metal. The reaction mixture is generally placed in a sealed pressure vessel, preferably lined with an inert plastic material such as polytetrafluoroethylene and heated, preferably under autogeneous pressure at an effective temperature which is preferably between about 100° C. (212° F.) and about 225° C. (424° F.), more preferably between 100° C. (212° C.) and 200° C. (424° F.), until crystals of the specific variety of QAPSO product are obtained, usually an effective crystallization time of from several hours to several weeks. Generally, effective crystallization times of from about 2 hours to about 30 days are employed with typically from 4 hours to about 20 days being employed to obtain the QAPSO product version. The product is recovered by any convenient method such as centrifugation or filtration.

In synthesizing the QAPSO compositions used in the instant invention, it is an preferred to employ a reaction mixture composition expressed in terms of molar ratios as follows:

> $aR:(Q_wAl_xP_ySi_z)O_2:bH_2O$ wherein "R" is an organic templating agent: "a" is the amount of organic templating agent "R" and has a value of from zero to about 6 and is preferably an effective amount within the range of greater than zero (0) to about 6; "b" has a value of from zero (0) to about 500, preferably between about 2 and about 300; "Q" represents at least one element, as hereinbefore described, capable of forming a framework oxide unit, $QO_2^n$, with $SiO_2$, $AlO_2^-$ and $PO_2^+$ tetrahedral oxide units; "n" has a value of $-3$, $-2$, $-1$, $0$ or $+1$; and "w", "x", "y", "z" are as defined above.

In the foregoing expression of the reaction composition, the reactants are normalized with respect to the total of "w", "x", "y", and "z" such that $w+x+y+z=1.00$ mole, whereas in the examples in the reaction mixtures may be expressed in terms of molar oxide ratios normalized to the moles of $P_2O_5$. This latter form is readily converted to the former form by routine calculations by dividing the number of moles of each component (including the template and water) by the total number of moles of elements "Q", aluminum, phosphorus and silicon which results in normalized mole fractions based on total moles of the aforementioned components.

In forming reaction mixtures from which the QAPSO molecular sieves are formed, an organic templating agent is preferably employed and may be any of those heretofore proposed for use in the synthesis of conventional zeolite aluminosilicates but, in any case, the template chosen is that template taught in the art for making the particular QAPSO being made. In general, these compounds contain elements of Group VA of the Periodic Table of Elements, particularly nitrogen, phosphorus, arsenic and antimony, preferably nitrogen or phosphorous and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter two being represented generally by the formula $R_4X^+$ wherein "X" is nitrogen or phosphorous and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents may be necessary or useful in producing a particular QAPSO. The initial gel pH in most cases is weakly acidic facilitating the successful incorporation of the hydrolyzable metal cation form of the elements into the frameworks, and inhibiting their precipitation as spurious hydroxides or oxides. Representative templating agents include: ammonium ions such as tetramethylammonium, tetraethylammonium, tetrapropylammonium, tetrabutylammonium, and tetrapentylammonium and amines such as di-n-propylamine, tripropylamine, triethylamine, triethanolamine, piperidine, cyclohexylamine, 2-methylpyridine, N,N-dimethylbenzylamine, N,N-dimethylethanolamine, choline, N,N'-dimethypiperazine, 1,4-diazabicyclo(2,2,2,)octane, N-methyldiethanolamine, N-methylethanolamine, N-methylpiperidine, 3-methylpiperidine, N-methylcyclohexylamine, 3-methylpyridine, 4-methylpyridine, quinuclidine, N,N'-dimethyl-1,4-diazabicyclo(2,2,2)octane, di-n-butylamine, neopentylamine, di-n-pentylamine, isopropylamine, t-butylamine, ethylenediamine, diethylenetriamine, triethylenetetraamine, pyrrolidine, 2-imidazolidone, and the like. Not every templating agent will direct the formation of every species of QAPSO, i.e., a single templating agent may, with proper manipulation of the reaction conditions, direct the formation of several QAPSO compositions, and a given QAPSO composition can be produced using several different templating agents.

As Flanigen et al., in the paper entitled Aluminophosphate Molecular Sieves and the Periodic Table, supra, point out:

"The organic template appears to play a critical structure-directing role. The template is trapped or clathrated in the structural voids as the crystals grow. Over eighty-five amines and quaternary ammoniumspecies have been used successfully as crystallization templates, including primary, secondary, tertiary and cyclic amines, and alkanolamines. The degree of template-structure specificity varies from the crystallization of AlPO₄-5 with twenty-three templates to the formation of AlPO₄-20 with only one template.[17]) Table 6, a summary of typical templates forming the major structures, amply illustrates one template forming many structures (11, 31, 41 and 46 with di-n-propylamine).

Here, structure control is exercised by other synthesis variables such as temperature, template concentration, gel oxide composition, and pH. The influence of the template is both steric and electronic, and typically exhibits the neat stoichiometry and space-filling characteristics illustrated for AlPO$_4$-5 and 11."

TABLE 6
Structure-Template Relationships

| Structure Type | Typical Template(s) |
|---|---|
| Large Pore | |
| 5 | tetrapropylammonium, tri-n-propylamine |
| 36 | tri-n-propylamine |
| 37 | tetrapropylammonium + tetramethylammonium |
| 46 | di-n-propylamine |
| Intermediate Pore | |
| 11 | di-n-propylamine, di-iso-propylamine |
| 31 | di-n-propylamine |
| 41 | di-n-propylamine |
| Small Pore | |
| 14 | isopropylamine |
| 17 | quinuclidine, piperidine |
| 18 | tetraethylammonium |
| 34 | tetraethylammonium |
| 35 | quinuclidine |
| 44 | cyclohexylamine |
| 47 | diethylethanolamine |
| Very Small Pore | |
| 20 | tetramethylammonium |

The foregoing description of the role of the templating agent is characteristic of the general role of templating agents in respect to the manufacture of the QAPSO family.

The source of silicon may be silica, either as a silica sol or as fumed silica, a reactive solid amorphous precipitated silica, silica gel, alkoxides of silicon, silica containing clays, silicic acid or alkali metal silicate and mixtures thereof.

The most suitable phosphorus source yet found for the aluminophosphates is phosphoric acid, but organic phosphates such as triethyl phosphate have been found satisfactory, and so also have crystalline or amorphous aluminophosphates such as the AlPO$_4$ compositions of U.S. Pat. No.. 4,310,440. Organo-phosphorus compounds, such as tetrabutylphosphonium bromide do not appear to serve as reactive sources of phosphorus, but these compounds do function as templating agents. Conventional phosphorus salts such as sodium metaphosphate, may be used, at least in part, as the phosphorus source, but are not preferred.

The preferred aluminum is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, aluminum-containing clays, sodium aluminate and aluminum trichloride, can be employed but are not preferred.

The element(s) "Q" can be introduced into the reaction system in any form which permits the formation in situ of a reactive form of the element, i.e., reactive to form a framework oxide unit of element "Q". Compounds of element(s) "Q" which may be employed include (but are not limited to) oxides, hydroxides, alkoxides, nitrates, sulfates, halides, carboxylates and mixtures thereof. Representative compounds which may be employed include inter alia: carboxylates of arsenic and beryllium; cobalt chloride hexahydrate, alpha cobaltous iodide; cobaltous sulfate; cobalt acetate; cobaltous bromide, cobaltous chloride; boron alkoxides; chromium acetate; gallium alkoxides; zinc acetate; zinc bromide; zinc formate; zinc iodide; zinc sulfate heptahydrate; germanium dioxide; iron (II) acetate; lithium acetate; magnesium acetate; magnesium bromide; magnesium chloride; magnesium iodide; magnesium nitrate; magnesium sulfate; manganese acetate; manganese bromide; manganese sulfate; titanium tetrachloride; titanium carboxylates; titanium acetate; zinc acetate; and the like.

After crystallization, the QAPSO product may be isolated and advantageously washed with water and dried in air. The as-synthesized QAPSO generally contains within its internal pore system at least one form of any templating agent employed in its formation. Most commonly, this organic moiety, derived from any organic template, is at least in part present as a charge-balancing cation, as generally is the case with as-synthesized aluminosilicate zeolites prepared from organic-containing reaction systems. It is possible, however, that some or all of the organic moiety may be an occluded molecular species in a particular QAPSO species. As a general rule the templating agent, and hence the occluded organic species, is too large to move freely through the pore system of the QAPSO product and must be removed by calcining the QAPSO at temperatures of 200° C. to 700° C. to thermally degrade the organic species. In some instances the pores of the QAPSO compositions are sufficiently large to permit transport of the templating agent, particularly if the latter is a small molecule, and accordingly complete or partial removal thereof may be accomplished by conventional desorption procedures such as carried out in the case of zeolites. It will be understood that the term "as-synthesized" as used herein does not include the condition of QAPSO species wherein any organic moiety occupying the intracrystalline pore system as a result of the hydrothermal crystallization process has been reduced by post-synthesis treatment such that the value of "m" in the composition formula:

mR:(Q$_w$Al$_x$P$_y$Si$_z$)O$_2$ has a value of less than 0.02. The other symbols of the formula are as defined hereinabove. In those preparations in which an alkoxide is employed as the source of element(s) "Q", aluminum, phosphorous and/or silicon, the corresponding alcohol is necessarily present in the reaction mixture since it is a hydrolysis product of the alkoxide. As has been reported repeatedly in the NZMS patent literature, it has not been determined whether this alcohol participates in the syntheses process as a templating agent. For the purposes of this application, however, this alcohol is arbitrarily omitted from the class of templating agents, even if it is present in the as-synthesized QAPSO material.

Since the present QAPSO compositions are formed from AlO$_2^-$, PO$_2^+$, SiO$_2$ and QO$_2^n$ framework oxide units which, respectively, has a net charge of $-1$, $+1$, 0 and "n", where "n" is $-3$, $-2$, $-1$, 0 or $+1$, the matter of cation exchangeability is considerably more complicated than in the case of zeolitic molecular sieves in which, ideally, there is a stoichiometric relationship between AlO$_2^-$ tetrahedra and charge-balancing cations. In the instant compositions, an AlO$_2^-$ tetrahedron can be balanced electrically either by association with a $PO_2^+$ tetrahedron or a simple cation such as an alkali metal cation or proton, a cation of the element "Q" present in the reaction mixture, or an organic cation derived from the templating agent. Similarly, an $QO_2^n$ oxide can be balanced electrically by association with $PO_2^+$ tetrahedra, a simple cation such as an alkali metal cation, a cation of the metal "Q", organic cations derived from the templating agent, or other divalent or polyvalent metal cations introduced from an extraneous source.

The QAPSO compositions may exhibit cation-exchange capacity when analyzed using ion-exchange techniques heretofore employed with zeolite aluminosilicates and have pore diameters which are inherent in the lattice structure of each species and which are at least about 3 Å in diameter. Dehydration to remove water present in the as-synthesized QAPSO compositions can usually be accomplished, to some degree at least, in the usual manner without removal of the organic moiety, but the absence of the organic species greatly facilitates adsorption and desorption procedures. The QAPSO materials will have various degrees of hydrothermal and thermal stability, some being quite remarkable in this regard, and will function as molecular sieve adsorbents and hydrocarbon conversion catalysts or catalyst bases.

Zeolite structures, used to make the composites of this invention, may be made free of contact with the QAPSO containing phase or in the presence of the QAPSO containing phase subject to the caveat about pH of the zeolite gel. They may be generated by the hydrothermal crystallization of an aluminate and silicate under basic conditions. Aqueous gels of the reactants are heated at temperatures ranging from about 50° C. (122° F.) to about 200° C. (392° F.), preferably from about 100° C. (212° F.) to about 175° C. (347° F.). The optimum crystallization temperature depends on composition and structure. A good characterization of processes for the manufacture of zeolites can be found at Chapter Four of Breck, *Zeolite Molecular Sieves*, Publ. by John Wiley & Sons, New York, N.Y., 1974 and at Chapter 11 by Magee and Blazek of Rabo, supra.

The composites of this invention are conveniently formed by the hydrothermal crystallization of one phase in the presence of the other or another. Broadly speaking, each phase of the composite is derived by the hydrothermal crystallization of the components thereof from an aqueous gel. The composite derives from the hydrothermal crystallization of the precursor to the formation of an intended phase in the presence of a deposition substrate which constitutes another phase of the composite. The deposition substrate need not be, in the practice of this invention, a fully formed (e.g., not fully crystallized) composition. Thus, one might initiate the production of a molecular sieve structure by the hydrothermal crystallization procedure, and prior to the fully formed crystal structure, such is utilized as a deposition substrate by the addition thereto of the precursors to be used for the manufacture of an outer layer. In such a case, the deposition substrate is termed to be in the "green" state. There will be instances where one will remove a cation or cations from the deposition substrate after depositing an outer layer thereon. Such cation removal can be effected after the deposition has been completed and a composite structure is formed.

A differential crystallization of one phase prior to another using a single gel that generates both phases is another method of forming a deposition substrate. Such a procedure works effectively when both phases are NZMSs and primarily differ by the presence or absence of Me or EL elements which generate MeAPO, MeAPSO, ELAPO or ELAPSO compositions.

The composites used in the invention do not depend upon the existence of a clear demarcation between the framework composition of one phase and another either during the manufacture of the composite or in the finished composite. As pointed out above, there is often a transformation occurring at the interface of the phases such that the interface could be viewed as constituting a nominal third framework phase of an intended two-phase system or fourth or fifth framework phase of an intended three-phase system. Indeed, one may look at the transition from the framework composition of one phase to another as a gradient compositional change existing between the phases though it is believed that the gradient is primarily differentiable at about the interface with the remainder of the phases being each more homogeneous compositionally. The compositional heterogeneity of the composites of this invention extends in a gross sense by virtue of a difference in the composition of the phases and in the relationship of a phase to the other in respect to the framework composition at the interface.

The hydrocrystallization conditions for synthesizing the composite is that cited above with respect to the specific molecular sieve composition intended for the phase undergoing hydrothermal crystallization. When a preformed zeolitic molecular sieve is used as a deposition substrate for the intended deposition of a non-zeolitic aluminum and phosphorus based molecular sieve then, of course, the hydrothermal crystallization of reactive aluminum and phosphorus gels in the presence of the zeolitic molecular sieve should be employed. This does not mean that the synthesis will yield a phase which mimics entirely the composition of molecular sieve which is intended by that hydrothermal crystallization synthesis. The compositions that are formed are believed to be different in subtle ways by what transpires at the interface, as indicated above, but similar enough so as to be embraced by the prior characterization of the composition of such a molecular sieve. Preferably, one of the phases, acting as a deposition substrate, is a fully formed crystalline structure. The template may or may not be essentially removed before the composition is subjected to contact with the components which are used to generate the other phase. The deposition substrate is a support for the next produced phase (outer layer) and provides the basis for epitaxial growth. Once one phase is crystallized in the presence of another crystal phase, the composite may be used as the support for the creation of still another solid phase. This procedure may be repeated as many times as desired or as there exists enough molecular sieves of different compositions but having the same crystalline framework to provide a composite of an essentially single crystal structure. By this technique, one may produce a composite having repeated layers of different molecular sieves in an onion skin pattern, except that in the case of the composites of this invention, the skins are chemically bonded to one another. There are occasions where one might wish to blend the ingredients of distinct molecular sieve compositions and effect the hydrothermal differential crystallization to form a mixed phase composition encompassed by this invention. In the typical case, the composites will be formed by the hydrothermal crystallization of a molecular sieve brew in contact with another but already formed or partially formed crystalline molecular sieve of appropriate crystalline structure.

It is believed that the composite is formed by the epitaxial growth of a crystal onto the surface of the deposition substrate. [It may be the case in some instances that this growth is facilitated by the deposition substrate. Such may be termed a "seeding" effect. However, that would be an insignificant consideration in comparison to the role of the deposition substrate in forming composites having unique and unexpected properties.] The growth in this manner yields a substrate support surface onto which a layer of crystalline molecular sieve is deposited and epitaxially grafts in the process of the hydrothermal crystallization to the crystal framework of the support surface. In this fashion, one may obtain a core surrounded or enveloped by a layer or a film or a mantle of the other molecular sieve(s). Membranes having a differential of exchange properties across the depth of the composite can be made from multi-layers of these films deposited over the core and onto each previously deposited layer. Composites which are multi-faceted in their performance can be made up of layers each of which has a different adsorption and catalytic characteristic.

There is the possibility that during hydrothermal crystallization of a phase in the presence of another already formed phase that some of the crystallization will result in particles free of composite formation, that is, the crystallization does not occur on the surface of the formed phase. Experience to date shows that little if any independent crystallization of that type occurs. In the usual case, not more than about 50 weight percent of the generated product of the hydrothermal crystallization will comprise such particles free of composite formation. More preferably, not more than about 25 weight percent, most preferably not more than about 5 weight percent, and most desirably (and usually) about 0 weight percent, of the generated product of the hydrothermal crystallization will comprise such particles free of composite formation.

As pointed out below, the shape of the composite is particulate but when used as an oligomerization catalyst, the use to which the composite will be put will determine its overall configuration. In the context of oligomerization catalysis, the composite may be used as formed or they may be combined either by a binderless process or by use of other ingredients and formed into a structure more desirable for the use. The particles can be formed into another shape by a variety of techniques well known in the art, such as by spray drying, combining the particles via a matrix binder, and the like. Catalysts will be made to properly configure to the shape of the reactor or the reaction mode. However, certain special effects can be obtained with the composite structures of this invention. For example, rather than deposit the outer layer onto the deposition surface prior to associating the composite with a matrix bonding media, the deposition substrate can first be shaped by spray drying or by combination with a matrix bonding media according to the use (viz., into pellets, extrudates, and the like) and then the shaped body containing the deposition substrate or surface is subjected to the hydrothermal crystallization in a brew of the precursors forming the outer layer. The outer layer is thus deposited on the deposition surface that remains exposed in the shaped body. This procedure minimizes the amount of outer layer required for a composite/matrix shaped product.

In the preferred embodiment, the composite is formed prior to the formation of a shaped body containing the composite.

As pointed out previously, the shape of the finished catalyst or absorbent particles formed from the composite is determined by the use to which it is put. It can be employed as such as the formed particles or the formed particles can be bonded to each other directly or indirectly through a binding medium to make a larger shaped catalyst in satisfaction of the intended catalyst use. In the most common case, composite particles will be bound together by a variety of techniques such as by spray drying, pelletizing, extrusion, and the like. A binder is typically used to shape the composite particles into predetermined pellets, spray-dried particles or extrudates, as one desires, using conventional techniques of the catalyst art. For example, composite particles may be blended with a matrix material, typically one that would be inert to the reactants of the catalytic process, and pelletized or extruded into the desired shape. The configuration of the composite of the invention is not critical to this invention, but can be important in respect to a particular use.

Oligomerization catalysts made from the composites of this invention are typically a physical blend of the composite with an inorganic oxide matrix component which may be any of the inorganic oxide matrix components which have been employed heretofore in the formulation of catalysts including: amorphous catalytic inorganic oxides, e.g., catalytically active silica-aluminas such as amorphous aluminosilicates and zeolites, clays, silicas, aluminas, silica-zirconias, silica-magnesias, alumina-borias, alumina-titanias and the like and mixtures thereof. The composite is usually mixed with the matrix component and then formed in the appropriate catalyst shape.

The inorganic oxide matrix components, e.g. aluminas, silicas, clays, etc., may be present in the final catalyst in an amount ranging between about 5 and about 99 weight percent, preferably between about 5 and about 95 weight percent and more preferably between about 10 and about 85 weight percent, based on the total catalyst weight.

The inorganic oxide matrix component may be in the form of a sol, hydrogel or gel and is typically an alumina, silica, clay and/or silica-alumina component such as employed in a conventional silica-alumina catalyst, several types and compositions of which are commercially available. The matrix component may itself provide a catalytic effect or it may be essentially inert. The matrix may act as a "binder" in some instances, although in some instances the final catalyst may be spray dried or formed without the need of a binder. These materials may be prepared as a cogel of silica and alumina or as alumina precipitated on a preformed and preaged hydrogel. The silica may be present as a component in the solids present in such gels, e.g., present in an amount between about 5 and about 40 weight percent and preferably between about 10 and about 35 weight percent. Silica may also be employed in the form of a cogel comprising about 75 weight percent silica and about 25 weight percent alumina or comprising about 87 weight percent silica and about 13 weight percent alumina.

The alumina component may comprise discrete particles of various aluminas, e.g., pseudobeohmite. The alumina component may be in the form of discrete particles having a total surface area, as measured by the method of Brunauer, Emmett and Teller (BET), greater than about 20 square meters per gram (m²/g), preferably greater than 145 m²/g, for example, from about 145 to about 300 m²/g. The pore volume of the alumina component is typically greater than 0.35 cc/g. The average particle size of the alumina particles is generally less than 10 microns and preferably less than 3 microns. The alumina may be employed alone as the matrix or composited with the other matrix components such as the silica, as mentioned previously. The alumina component may be any alumina and, preferably, has been preformed and placed in a physical form such that its surface area and pore structure are stabilized. This means that when the alumina is added to an impure, inorganic gel containing considerable amounts of residual soluble salts, the salts will not alter the surface and pore characteristics measurably nor will they promote chemical attack on the preformed porous alumina which could undergo change. For example, the alumina may be an alumina which has been formed by suitable chemical reaction, slurry aged, filtered, dried, washed free of residual salt and then heated to reduce its volatile content to less than about 15 weight percent. Further, an alumina hydrosol or hydrogel or hydrous alumina slurry may be used in the catalyst preparation.

Mixtures of the composite particles and the inorganic matrix may be formed into the final form for the catalyst by standard catalyst forming techniques including spray-drying, pelleting, extrusion and other suitable conventional means. Such catalysts are typically prepared by spray drying, such procedures being well known to those skilled in the art of preparing catalysts.

Illustrative of the procedures for making catalysts from the composites of this invention is the following: Sodium silicate is reacted with a solution of aluminum sulfate to form a silica/alumina hydrogel slurry which is then aged to give the desired pore properties, filtered to remove a considerable amount of the extraneous and undesired sodium and sulfate ions and then reslurried in water. The alumina may be prepared by reacting solutions of sodium aluminate and aluminum sulfate under suitable conditions, aging the slurry to give the desired pore properties of the alumina, filtering drying, reslurry in water to remove sodium and sulfate ions and drying to reduce volatile matter content to less than 15 weight percent. The alumina may then be slurried in water and blended in proper amounts, with a slurry of impure silica-alumina hydrogel. The composite molecular sieve may then be added to this blend. A sufficient amount of each component is utilized to give the desired final composition. The resulting mixture is then filtered to remove a portion of the remaining extraneous soluble salts therefrom. The filtered mixture is then dried to produce dried solids. The dried solids are subsequently reslurried in water and washed substantially free of the undesired soluble salts. The catalyst is then dried to a residual water content of less than about 15 weight percent. The catalyst is typically recovered after calcination.

It is also within the scope of the instant invention to employ other materials in addition to the composite and inorganic oxide matrix components in the final catalysts, including various other types of zeolites, clays, carbon monoxide oxidation promoters, etc.

Representative of matrix systems employable herein are disclosed in British Patent Specification No. 1,315,553, published May 2, 1973 and U.S. Pat. Nos. 3,446,727 and 4,086,187, such being incorporated herein by reference thereto.

In order to more particularly illustrate this invention, specific reference will be made to embodiments thereof. It is not intended that such should act to limit the scope of the invention.

In the examples, a stainless steel reaction vessel is utilized which is lined with an inert plastic material, polytetrafluorethylene, to avoid contamination of the reaction mixture. In general, the final reaction mixture, from which the composite is crystallized, is prepared by forming mixtures of all of the reagents before adding the deposition substrate, then adding the deposition substrate. Conversely, the deposition substrate may be first added to a reactor and then the reagents for forming the hydrogel which generates the outer layer may be added. Hydrothermal crystallization thereafter follows. There are conditions where the reagents of a phase result in hydrothermal crystallization kinetics which are different from those produce by the reagents of another phase. In that situation, the reagents can be combined at the same time and the difference in kinetics provides a deposition substrate for crystal growth. Such is termed "differential crystallization" herein. In some instances the admixed reagents retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially uniform.

Table F which follows provides a match of different phases that are combinable to make preferred composite catalysts suitable for this invention.

TABLE F

MATCHED PHASES

| | | | | The "Other Phases" | | | |
|---|---|---|---|---|---|---|---|
| Structure Type | One Phase | AlPO$_4$ | SAPO | MeAPO (Me = Co, Fe, Mg, Mn, Zn) | MeAPSO (Me = Co, Fe, Mg, Mn, Zn) | ELAPO (EL = As, Be, B Cr, Ga, Ge, Li, V, Ti) | ELAPSO (EL = As, Be, B Cr, Ga, Ge, Li, V, Ti) |
| | Intermediate Pore | | | | | | |
| 11 | " | X | X | X | X | X | X |
| 31 | " | X | X | X | X | X | X |
| 40 | " | X | X | X | X | X | X |
| 41 | " | X | X | X | X | X | X |
| | Small Pore | | | | | | |
| 14 | " | X | X | X | X | X | X |
| 17 | " + erionite | X | X | X | X | X | X |
| 18 | From "Other Phases" | X | X | X | X | X | X |
| 33 | " | X | X | X | X | X | X |
| 34 | " + chabazite | X | X | X | X | X | X |
| 35 | " + levynite | X | X | X | X | X | X |
| 39 | From "Other Phases" | X | X | X | X | X | X |

TABLE F-continued

MATCHED PHASES

| | | | | The "Other Phases" | | | |
|---|---|---|---|---|---|---|---|
| Structure Type | One Phase | AlPO₄ | SAPO | MeAPO (Me = Co, Fe, Mg, Mn, Zn) | MeAPSO (Me = Co, Fe, Mg, Mn, Zn) | ELAPO (EL = As, Be, B Cr, Ga, Ge, Li, V, Ti) | ELAPSO (EL = As, Be, B Cr, Ga, Ge, Li, V, Ti) |
| 42 | " + Linde type A | — | X | — | — | X | X |
| 43 | From "Other Phases" + gismondine | — | X | X | X | X | X |
| 44 | From "Other Phases" + chabazite-like | — | X | X | X | X | X |
| 47 | From "Other Phases" + | — | — | X | X | X | X |

As an illustration of the broad variety of composites embraced by this invention, the following Table G illustrates, by constructive reduction, two-phase composites utilizing the techniques described herein of depositing one molecular sieve as an outer layer onto a deposition substrate of another molecular sieve by the hydrothermal crystallization process.

The composites in Table G use the designated molecular sieve deposition substrates and outer layers. Each deposition substrate is preformed using the procedures disclosed in the referenced prior art. The outer layers are made according to the following general procedure, to be modified in accordance with the referenced prior art. The general procedure is as follows:

The gel is prepared by dissolving in a first container the indicated amount of the templating agent cited in the referenced prior art. This is followed by the addition of the indicated amount of the silica source, if used, and if not used, the aluminum and phosphorus sources, in accordance with the referenced prior art. If a silica is used, then in a second container, the indicated amount cited by the referenced prior art of a hydrated aluminum oxide (such as a pseudo-boehmite phase, 74.2 wt. % Al₂O₃ 25.8 wt. % H₂O), the indicated amount of the phosphorus source, such as phosphoric acid (85%), the indicated amount of the metal salt, and a specified amount of water, are thoroughly mixed. In the next step, the mixture in the first container is added to the alumina, phosphoric acid and metal salt (if employed) slurry in the second container and the combination is mixed for an additional period of time to form a gel that would be used to treat the deposition substrate. If only one container is employed, then the contents are appropriately mixed until the gel consistency is achieved.

In forming the composite, a thorough mixture of the gel and the deposition substrate are placed in a 250 cc polytetrafluoroethylene-lined, stainless steel reactor and digested quiescently (without operation of the stirrer) for about 5 to 24 hours at 200° C. The composite product of the digestion is cooled, and the supernatant liquid present is decanted. The solid product is washed several times in water and finally air dried.

The weight ratios cited in Table G is of the deposition substrate phase to the outer layer.

TABLE G

| Outer Layer | Deposition Phase | Weight Ratios[9] |
|---|---|---|
| | Intermediate Pore | |
| SAPO-11[10] | AlPO-11[11] | 1 |
| SAPO-31[12] | AlPO-31[13] | 2 |
| SAPO-41[14] | AlPO-41[15] | 1.22 |
| MnAPSO-11[16] | AlPO-11 | 1 |
| ZnAPSO-11[17] | AlPO-11 | 2.33 |
| MnAPSO-11 | ZnAPO-11[18] | 3 |
| CoAPSO-11[19] | ZnAPO-11 | 5 |
| CoAPSO-11[20] | AlPO-11 | 3 |

TABLE G-continued

| Outer Layer | Deposition Phase | Weight Ratios[9] |
|---|---|---|
| CoAPSO-31[21] | AlPO-31 | 3 |
| MnAPO-11[22] | AlPO-11 | 1 |
| MnAPSO-31[23] | AlPO-31 | 1.5 |
| CoAPSO 11[24] | AlPO-11 | 8 |
| CoAPSO-41[25] | AlPO-41 | 4 |
| SAPO-31 | CoAPO-31[26] | 2 |
| SAPO-11 | CoAPSO-11 | .5 |
| SAPO-11 | CoApO-11 | 1 |
| FeAPO-11 | SAPO-11 | 1 |
| SAPO-11 | FeAPO-11 | 1 |
| SAPO-11 | AlPO-11 | 3 |
| CoAPSO-31 | AlPO-31 | 2 |
| SAPO-31 | AlPO-31 | 1 |
| | Small Pores | |
| SAPO-34[27] | AlPO-34[28] | 2 |
| SAPO-34[27] | acid washed chabasite | 1 |
| CoAPSO-34[29] | AlPO-34 | 5.67 |
| MnAPSO-34[30] | AlPO-34 | 2 |
| SAPO-17[31] | Erionite | 1 |
| SAPO-17[31] | AlPO-17[32] | .95 |
| ZnAPO-11[33] | MnAPO-11[34] | 1 |

[9]Weight ratio of deposition substrate to outer layer, ie. deposition substrate / outer layer
[10]See Examples 15-22 of U.S. Pat. No. 4,440,871.
[11]See Examples 32-36 of U.S. Pat. No. 4,310,440.
[12]See Examples 51-3 of U.S. Pat. No. 4,440,871.
[13]See Example 54 of U.S. Pat. No. 4,310,440.
[14]See Example 54 of U.S. Pat. No. 4,440,871.
[15]See copending U.S. Pat. application Ser. No. 880,059, filed 1986, commonly assigned.
[16]See Examples 24-27 of European Patent Publication 0 161 490.
[17]See Examples 10 and 11 of European Patent Publication 0 158 975
[18]See Examples 55, 56 of U.S. Pat. No. 4,567,029.
[19]See Examples 32-35, 37, 38, 40-45 and 49-53 of European Publication 0 161 489
[20]See Examples 93-95 of U.S. Pat. No. 4,567,029.
[21]See Examples 97 and 99-103 of European Publication 0 161 489
[22]See Examples 72-75 of U.S. Pat. No. 4,567,029.
[23]See Examples 50-56 of European Patent Publication 0 161 490.
[24]See Examples 32-35, 37, 38, 40-45 and 49-53 of European Publication 0 161 489.
[25]See Example 11 below for preparation of CoAPSO-41.
[26]See Example 10 below for preparation of CoAPO-31.
[27]See Examples 32-38 of U.S. Pat. No. 4,440,871 for preparation.
[28]See example 12 below for the preparation of ALPO-34.
[29]See Examples 84-90 of European Patent Publication 0 161 489 for preparation.
[30]See Examples 6-8, 11, and 12 of European Patent Publication 0 161 490 for preparation.
[31]See Examples 25-26 of U.S. Pat. No. 4,440,871 for preparation.
[32]See Examples 42-45 of U.S. Pat. No. 4,310,440 for preparation.
[33]See examples 55-56 of U.S. Pat. No. 4,567,029.
[34]See examples 72-75 of U.S. Pat. No. 4,567,029.

In addition to the foregoing detailed characterization of this invention, the following enumerated examples serve to further define this invention.

EXAMPLE 1

(a) To a solution of 40.4 grams 85 weight % orthophosphoric acid (H₃PO₄) in 133.2 grams H₂O was slowly added 17.7 grams of di-n-propylamine (DPA) and 18.4 grams of diethanolamine (DEA). The liquids were stirred until miscible and allowed to cool to ambient temperature. Into this solution was mixed 4.8 grams HiSil (precipitated silica, 88 wt. % SiO₂, 12 wt % H₂O)

followed by the admixture of 25.9 grams of hydrated alumina (pseudo-boehmite phase, 70 wt. % $Al_2O_3$, 30 wt. % $H_2O$). The resulting mixture was blended until homogeneous. The elemental composition of this mixture expressed in molar oxide ratios was: 1.0 DPA: 1.0 DEA: 0.4 $SiO_2$: $Al_2O_3$: $P_2O_5$: 50 $H_2O$ (b) 48.4 grams of an as synthesized $AlPO_4$-11 with an elemental composition of:

0.18 DPA: $Al_2O_3$: $P_2O_5$:0.8 $H_2O$ was ground up gently in a mortar and pestle, then slurried in 100 grams $H_2O$. This $AlPO_4$-11 slurry was added quickly to the mixture of (a). An additional 23 grams of $H_2O$ was reserved to use in completely transferring all of the $AlPO_4$-11 into the final mixture. The elemental composition of the final mixture expressed in molar oxide ratios was:

0.6 DPA: 0.5 DEA: 0.2 $SiO_2$: $Al_2O_3$: $P_2O_5$: 45 $H_2O$

The final mixture was loaded into a stainless steel pressure vessel equipped for stirring and it was heated to 175° C. over a 2 hour period. The reaction mixture was maintained at 175° C. for 24 hours then cooled. The product was allowed to settle for 72 hours and the supernatant mother liquor was decanted. The solids were resuspended in fresh water and allowed to settle for 1hour. The cloudy supernatant was decanted and recovered by centrifugation. The settled solids were recovered by filtration.

(c) The weights of the recovered products were:

| | |
|---|---|
| Solids from supernatant liquid | 57.4 grams |
| Settled solids | 20.3 grams |

There was recovered 29.9 grams of additional material over the 48.4 grams of the starting $AlPO_4$-11. This indicated that the SAPO-11 outer layer was about 38 weight % of the composite structure. X-ray analysis of the two product fractions showed that the settled solids were pure 11-type (SAPO-11 composited on $AlPO_4$-11) and the solids recovered from the supernatant liquid were primarily 11-type (SAPO-11 composited on $AlPO_4$-11) with a trace of the -41 structure-type.

(d) A sample of the settled solids was calcined in air at 500° C. for 16 hours and then tested for n-butane cracking activity as described above. It exhibited a $K_A$ of 0.2.

(e) A sample of settled solids exhibited the following elemental analysis, expressed in weight percents:

TABLE H

| | |
|---|---|
| $Al_2O_3$ | 37.2 |
| $P_2O_5$ | 46.5 |
| $SiO_2$ | 1.9 |
| Carbon | 5.3 |
| Nitrogen | 1.0 |
| Loss on Ignition | 13.8 |

(f) A sample of the settled solids was calcined in air at 600° C. for 3 hours. Adsorption capacities were measured on a standard McBain-Bakr gravimetric adsorption apparatus following vacuum activation at 350° C., and the following results were obtained:

TABLE I

| Adsorbate | Pressure, torr | Temp. | Weight % |
|---|---|---|---|
| Oxygen | 100 | −183° C. | 9.5 |

TABLE I-continued

| Adsorbate | Pressure, torr | Temp. | Weight % |
|---|---|---|---|
| Oxygen | 700 | −183° C. | 12.4 |
| Cyclohexane | 50 | 23° C. | 6.5 |

(g) Particle size analyses were carried out on the as synthesized $AlPO_4$-11 added to the initial reaction mixture and the settled solids of the SAPO-11/$AlPO_4$-11 composite. The median particle size of the $AlPO_4$-11 was 3.5 microns and the median particle size of the SAPO-11/$AlPO_4$-11 composite was 4.8 microns.

EXAMPLE 2

This example shows the manufacture of a composite of an outer layer of SAPO-11 deposited on and enveloping particles of $AlPO_4$-11 as the deposition substrate. An aluminophosphate precursor reaction mixture was prepared by combining 101.2 grams of 85 wt % orthophosphoric acid and 79.5 grams of distilled water, to which was added 69.8 grams of a hydrated aluminum oxide (a psuedo-boehmite phase, 74.4 wt. % $Al_2O_3$, 25.6 wt. % $H_2O$) with high speed stirring to form a homogenous gel. To this gel was added a mixture containing 19.4 grams of fumed silica (92.8 wt. % $SiO_2$, 7.2 wt. % $H_2O$) in 500 grams of a solution of 25.0 wt % tetra-n-butylammonium hydroxide (TBAOH) in methanol. The resulting silicoaluminophosphate gel combination was stirred thoroughly and while stirring 101.2 grams of di-n-propylamine was added. The composition of this reaction mixture in oxide molar ratio was:

2.0$Pr_2NH$ :0.5 $(TBA)_2O$: $Al_2O_3$: $P_2O_5$: 0.6 $SiO_2$: 16.75 $H_2O$: 24.3 $CH_3OH$

The total gel weight was approximately 690 grams and at a pH of 9.4. The gel was divided into 5 batches of approximately 137 grams each. Five equal portions of 15 grams each of an uncalcined $AlPO_4$-11 molecular sieve (85% solids, 15% $H_2O$) was added to each 137 grams batch of the SAPO-11 gel. Each batch was then homogenized by stirring and transferred to a 250 cc. polytetrafluoroethylene-lined pipe bomb. The pH (9.5) of each batch of this new deposition substrate containing gel reaction mixture did not change much. The bombs were placed in an oven already equilibrated at 200° C. and digested for 2, 4, 6 and 24 hours, respectively, with the 6 hour preparation being duplicated. The five bombs were in this manner subjected to a digestion period. After the desired digestion time, each bomb was removed from the oven and allowed to cool to room temperature. The reaction mixture in each bomb was centrifuged to remove the solids and the solids were dispersed in distilled water and centrifuged to remove unreacted materials. This washing procedure was repeated, the washed solids were recovered and dried at 100° C.

The $AlPO_4$-11 which had been added and the composite products produced were analyzed to contain the following components on a solids basis:

TABLE J

| Type | Time of Digestion | WT % | | |
| | | $Al_2O_3$ | $SiO_2$ | $P_2O_5$ |
|---|---|---|---|---|
| $AlPO_4$-11 | — | 41.2 | 0.0 | 58.8 |
| SAPO-11/$AlPO_4$-11 | 2 Hrs | 40.9 | 1.2 | 58.4 |
| SAPO-11/$AlPO_4$-11 | 4 Hrs | 40.2 | 2.0 | 58.3 |
| SAPO-11/$AlPO_4$-11 | 6 Hrs | 40.1 | 2.8 | 57.9 |
| SAPO-11/$AlPO_4$-11 | 24 Hrs | 38.5 | 4.6 | 57.2 |

Note the increase in SiO$_2$ content relative to deposition substrate as the time of digestion increased from 2 to 24 hours. This corresponds to the amount of deposition of the SAPO-11 outer layer on the silica free AlPO$_4$-11 deposition phase.

All products had been subjected to X-ray powder diffraction analysis and found to have the diffraction patterns typical of AlPO$_4$-11 AND SAPO-11. from 2 to 24 hours. This corresponds to the amount of deposition of the SAPO-11 outer layer on the silica free AlPO$_4$-11 deposition phase.

All products had been subjected to X-ray powder diffraction analysis and found to have the diffraction patterns typical of AlPO4-11 AND SAPO-11.

EXAMPLE 3

This example demonstrates the catalytic efficacy of a SAPO-11/AlPO$_4$-11 composite made according to the procedure of example 1, supra, digested for 4 hours, in oligomerizing ethylene. The oligomerization of ethylene to heavier olefins was effected in a microreactor according to the following procedure:

A portion of a "4 hours" SAPO-11/AlPO$_4$-11 composite made according to the procedure of example 1was calcined in air for over 2 hours at a temperature over 500° C., at a temperature sufficient to remove essentially all of the templates incorporated during synthesis. One gram of this activated composite, in the form of a powder, was blended with 3 grams of quartz chips and loaded into a tubular reactor which in turn was placed in a sand bath heat source. The reactor inlet was connected to a feed delivery system capable of delivering feed streams at controlled pressure and flow rate. The reactor outlet was connected to product collection system which contained a dry test meter to measure the volume of gas exiting the reactor and a on-line gas chromatograph capable of analyzing all products of interest (all C$_1$ to C$_6$ paraffins and olefins). The reactor was purged with nitrogen, pressurized to the reaction pressure of 350 psig. and heated to near the reaction temperature of 427° C. (800° F.). When the reaction temperature was reached, the nitrogen purge was stopped and a feed consisting of 14 weight % ethylene in nitrogen was passed over the catalyst at a flow rate of 198 cc./min. while maintaining the reaction pressure and reaction temperature. The reactor effluent was analyzed and used to calculate the % of ethylene converted to oligomerized products. For comparison purposes, a sample of SAPO-11 prepared according to U.S. Pat. No. 4,440,871, was tested under identical conditions. The results of both tests are summarized in the following:

TABLE K

| Catalyst | SAPO-11 | SAPO-11/AlPO$_4$-11 |
|---|---|---|
| % Oligomerization | 18.3 | 34.1 |

These results show that this composite is a significantly more active oligomerization catalyst than the SAPO-11.

EXAMPLE 4

This example demonstrates the manufacture of a composite in which AlPO$_4$-11 was deposited on SAPO-11. A reaction mixture was prepared by combining 6.87 grams of a hydrated aluminum oxide (a psuedo-boehmite phase, 74.4 wt % Al$_2$O$_3$, 25 wt % H$_2$O) with a diluted solution of 11.53 grams of 85 wt. % ortho-phosphoric acid (H$_3$PO$_4$) and 3.0 grams of distilled water. To this was added 5.06 grams of di-isopropylamine and the solution was mixed thoroughly. Approximately 22 grams of already synthesized SAPO-11 (see Examples 32–36 of U.S. Pat. No. 4,310,440) slurried in 40 cc. of distilled water was added to the AlPO$_4$-11 gel and the combination was mixed for 15 minutes using a high speed stirrer. The AlPO$_4$-11 gel containing the SAPO-11 was put into a polytetrafluoroethylene-lined 250 cc. pipe bomb. The reaction mixture was digested at 200° C. for 24 hours by placing the bomb in an oven maintained at 200° C. The yield of AlPO$_4$-11 from the gel employed was expected to be about 4.4 grams based on previous preparations of AlPO$_4$-11 made without the use of SAPO-11. After digestion, the bomb was removed from the oven and allowed to cool to room temperature. The reacted mixture was centrifuged at high speed and the solids collected. The solids were re-dispersed in distilled water and centrifuged once more to remove unreacted materials. This washing procedure was repeated one more time, and the solids recovered and dried at 100° C.

The SAPO-11 deposition substrate used in this preparation was analyzed to contain 38.8% Al$_2$O$_3$, 8.1% SiO$_2$ and 51.5% P$_2$O$_5$ based on the inorganic oxide solids basis. The AlPO$_4$-11/SAPO-11 composite product obtained was analyzed to contain 41.9% Al$_2$O$_3$, 3.7% SiO$_2$ and 53.3% P$_2$O$_5$ base on the same solids basis. The product had an X-ray powder diffraction pattern typical of SAPO-11 and AlPO$_4$-11 and indicated that the product was 129% crystalline relative to the starting SAPO-11 deposition substrate.

EXAMPLE 5

This example demonstrates the manufacture of a SAPO-31/AlPO$_4$-31 composite.

(a) An initial mixture was prepared by adding 34.8 grams of 85% orthophosphoric acid in 75.7 grams H$_2$O to 21.7 grams of hydrated aluminum oxide (a pseudo-boehmite phase, 70.6 wt. % Al$_2$O$_3$, 29.4 wt. % H$_2$O). To this initial mixture, 18.1 grams of an aqueous silica sol (30.1 wt. % SiO$_2$) was added, followed by 22.8 grams of n-ethylbutylamine (ETBUTN). This reaction mixture had the following composition in terms of molar oxide ratios:

15 ETBUTN: 1.0 Al$_2$O$_3$: 1. P$_2$O$_5$: 0.6 SiO$_2$: 40 H$_2$O.

This reaction mixture was divided into three equal parts. One of these portions was combined with 4.0 grams of pre-formed AlPO$_4$-31, which is equivalent to a 14:1 weight ratio by weight of reaction mixture to AlPO$_4$-31. The reaction mixture was placed in a sealed stainless steel pressure vessel lined with polytetrafluoroethylene and heated in an oven at 200° C. for six (6) hours. The solids were recovered by centrifugation, washed with distilled water, and dried at 100° C. The reaction yielded 14.0 grams of product, indicating an AlPO$_4$-31:total product weight ratio of 4.0:14.0. The solids were subjected to chemical analysis and the chemical composition was found to be 36.6 wt. % Al$_2$O$_3$, 45.2 wt. % P$_2$O$_5$, 6.8 wt. % SiO$_2$, 4.5 wt. % C, 0.9 wt. % N, and 11.5 wt. % LOI.

The following is the x-ray powder diffraction pattern data for the analyzed sample:

TABLE L

| PEAK # | BY HEIGHT | | BY AREA | | PEAK AREA | PEAK HEIGHT | REL. INT. |
|---|---|---|---|---|---|---|---|
| | ANGLE 2-theta | d-spacing | ANGLE 2-theta | d-spacing | | | |
| 1 | 7.7 | 11.5 | 7.6 | 11.65 | 537 | 56 | 1.7 |
| 2 | 8.5 | 10.4 | 8.4 | 10.5 | 46038 | 3205 | 95.4 |
| 3 | 14.8 | 6.0 | 14.7 | 6.01 | 933 | 48 | 1.4 |
| 4 | 17.1 | 5.2 | 17.0 | 5.205 | 3117 | 221 | 6.6 |
| 5 | 18.3 | 4.85 | 18.3 | 4.85 | 84 | 59 | 1.8 |
| 6 | 20.3 | 4.4 | 20.2 | 4.39 | 12224 | 627 | 18.7 |
| 7 | 22.0 | 4.06 | 21.9 | 4.06 | 8282 | 394 | 11.7 |
| 8 | 22.6 | 3.9 | 22.6 | 3.935 | 54754 | 3360 | 100.0 |
| 9 | 25.2 | 3.5 | 25.1 | 3.55 | 1278 | 64 | 1.9 |
| 10 | 25.7 | 3.5 | 25.7 | 3.47 | 2223 | 125 | 3.7 |
| 11 | 27.9 | 3.2 | 27.9 | 3.20 | 3903 | 182 | 5.4 |
| 12 | 28.3 | 3.15 | 28.3 | 3.15 | 706 | 68 | 2.0 |
| 13 | 29.7 | 3.00 | 29.7 | 3.00 | 3449 | 178 | 5.3 |
| 14 | 31.8 | 2.8 | 31.7 | 2.82 | 8278 | 279 | 8.3 |
| 15 | 34.65 | 2.6 | 34.6 | 2.595 | 520 | 47 | 1.4 |
| 16 | 35.15 | 2.55 | 35.1 | 2.56 | 3105 | 147 | 4.4 |
| 17 | 35.6 | 2.5 | 35.7 | 2.52 | 827 | 49 | 1.5 |
| 18 | 37.7 | 2.4 | 37.7 | 2.39 | 1259 | 66 | 2.0 |
| 19 | 37.9 | 2.4 | 37.9 | 2.37 | 548 | 59 | 1.8 |
| 20 | 38.2 | 2.4 | 38.2 | 2.36 | 544 | 46 | 1.4 |
| 21 | 39.4 | 2.3 | 39.3 | 2.29 | 1408 | 64 | 1.9 |
| 22 | 39.7 | 2.3 | 39.7 | 2.27 | 1089 | 66 | 2.0 |
| 23 | 40.1 | 2.25 | 40.1 | 2.25 | 513 | 47 | 1.4 |
| 24 | 45.3 | 2.0 | 49.1 | 1.86 | 998 | 36 | 1.1 |
| 25 | 46.2 | 2.0 | 46.15 | 1.97 | 440 | 44 | 1.3 |
| 26 | 46.3 | 2.0 | 46.3 | 1.96 | 336 | 40 | 1.2 |
| 27 | 46.6 | 2.0 | 46.65 | 1.95 | 692 | 51 | 1.5 |
| 28 | 48.3 | 1.9 | 48.3 | 1.88 | 495 | 36 | 1.1 |
| 29 | 48.7 | 1.9 | 48.6 | 1.87 | 1099 | 58 | 1.8 |
| 30 | 49.0 | 1.9 | 49.0 | 1.86 | 589 | 48 | 1.4 |
| 31 | 51.6 | 1.8 | 51.6 | 1.77 | 1139 | 74 | 2.2 |
| 32 | 51.7 | 1.8 | 51.8 | 1.77 | 874 | 73 | 2.2 |

(b) A portion of the solids in part (a) above was calcined at 600° C. for one (1) hour, and utilized in adsorption capacity studies using a standard McBain-Bakr gravimetric adsorption apparatus. After overnight activation at 360° C., the following data were obtained:

TABLE M

| Absorbate | Kinetic Diameter, Å | Pressure Torr | Temp., °C. | wt. % Adsorbed |
|---|---|---|---|---|
| $O_2$ | 3.46 | 100.0 | −183 | 7.4 |
| $O_2$ | 3.46 | 705.0 | −183 | 14.2 |
| neopentane | 6.2 | 101.0 | 22.7 | 4.1 |
| neopentane | 6.2 | 748.0 | 22.7 | 7.0 |
| n-hexane | 4.3 | 44.6 | 22.9 | 6.2 |
| $H_2O$ | 2.65 | 4.6 | 23.0 | 4.3 |
| $H_2O$ | 2.65 | 23.0 | 22.7 | 24.9 |

The pore size of the calcined product is greater than 6.2 Å as shown by adsorption of the neopentane, kinetic diameter of 6.2 Å. X-ray analysis of the SAPO-31/AlPO$_4$-31 composite sample used in the adsorption studies established that the x-ray diffraction pattern was essentially unchanged as a result of contact with the adsorbate species.

(c) A portion of the calcined material from part (b) above was used in a test designed to show utility as a catalyst for hydrocarbon cracking. A 1.64 gram portion was reacted with a 2 mole % n-butane in helium stream at 500° C. and about 50 cm³/min. (STP) flow rate for 50 minutes. The pseudo-first-order rate constant ($k_A$) for butane consumption was 0.8.

EXAMPLE 6

This example demonstrates the manufacture of a SAPO-31/AlPO$_4$-31 composite.

(a) An initial mixture was prepared by adding 46.8 grams of 85% orthophosphoric acid in 100.8 grams $H_2O$ to 28.9 grams of hydrated aluminum oxide (a pseudo-boehmite phase, 70.6 wt. % $Al_2O_3$, 29.4 wt. % $H_2O$). To this initial mixture 24.0 grams of an aqueous silica sol (Ludox TM-LS, 30.1 wt. % $SiO_2$) was added, followed by 30.5 grams of n-ethylbutylamine (ETBUTN). The reaction mixture had the following composition in terms of molar oxide ratios:

1.5 ETBUTN: 1.0 $Al_2O_3$: 1.0 $P_2O_5$: 0.6 $SiO_2$: 40 $H_2O$.

A 40.0 gram portion of this reaction mixture was mixed with 6.2 grams of AlPO$_4$-31, which is equivalent to a 6.45:1 ratio by weight of reaction mixture to AlPO$_4$-31.

The reaction mixture was placed in a sealed stainless steel pressure vessel lined with polytetrafluoroethylene and heated in an oven at 200° C. for three (3) hours. The solids were recovered by centrifugation, washed with water, and dried at 100° C. The reaction yielded 12.9 grams of product, indicating a deposition substrate:total product ratio of 6.2:12.9. The solids were subjected to chemical analysis and the chemical composition was found to be 37.2 wt. % $Al_2O_3$, 47.0 wt. % $P_2O_5$ 4.5 wt. % $SiO_2$, 4.0 wt. % C, 0.8 wt. % N and 10.7 wt. % LOI.

The x-ray powder diffraction pattern data of the analyzed sample is as follows:

TABLE N

| PEAK # | BY HEIGHT | | BY AREA | | PEAK AREA | PEAK HEIGHT | REL. INT. |
|---|---|---|---|---|---|---|---|
| | ANGLE 2-theta | d-spacing | ANGLE 2-theta | d-spacing | | | |
| 1 | 8.5 | 10.4 | 8.45 | 10.5 | 49194 | 3358 | 94.9 |
| 2 | 14.8 | 5.99 | 14.7 | 6.01 | 1364 | 67 | 1.9 |
| 3 | 17.1 | 5.2 | 17.0 | 5.20 | 3357 | 239 | 6.8 |
| 4 | 18.3 | 4.85 | 18.3 | 4.85 | 947 | 66 | 19 |
| 5 | 20.0 | 4.44 | 19.9 | 4.46 | 2820 | 263 | 7.4 |
| 6 | 20.3 | 4.37 | 20.3 | 4.38 | 9348 | 614 | 17.4 |
| 7 | 20.7 | 4.29 | 20.7 | 4.29 | 417 | 41 | 1.2 |
| 8 | 21.95 | 4.05 | 21.8 | 4.07 | 7324 | 336 | 9.5 |
| 9 | 22.65 | 3.93 | 22.6 | 3.93 | 61205 | 3539 | 100.0 |
| 10 | 23.5 | 3.79 | 23.5 | 3.79 | 36 | 35 | 1.0 |
| 11 | 25.3 | 3.3 | 2.2 | 3.53 | 1165 | 70 | 2.0 |
| 12 | 25.7 | 3.46 | 25.7 | 3.47 | 308 | 133 | 3.8 |
| 13 | 27.5 | 3.24 | 27. | 3.25 | 285 | 43 | 1.2 |
| 14 | 27.85 | 3.20 | 27.8 | 3.21 | 2792 | 151 | 4.3 |
| 15 | 28.3 | 3.15 | 28.3 | 3.16 | 679 | 78 | 2.2 |
| 16 | 28.4 | 3.15 | 28.4 | 3.15 | 621 | 77 | 2.2 |
| 17 | 29.8 | 2.995 | 29.8 | 3.00 | 3920 | 179 | 5.1 |
| 18 | 31.5 | 2.84 | 31.3 | 2.86 | 2664 | 151 | 4.3 |
| 19 | 31.8 | 2.81 | 31.8 | 2.81 | 888 | 252 | 7.1 |
| 20 | 34.7 | 2.59 | 34.6 | 2.59 | 93 | 57 | 1.6 |
| 21 | 35.1 | 2.55 | 3.1 | 2.56 | 3062 | 140 | 4.0 |
| 22 | 35.6 | 2.52 | 35.55 | 2.56 | 713 | 61 | 1.7 |
| 23 | 35.8 | 2.51 | 36.3 | 2.47 | 949 | 43 | 1.2 |
| 24 | 37.4 | 2.405 | 37.4 | 2.40 | 96 | 39 | 1.1 |
| 25 | 37.8 | 2.38 | 37.7 | 2.39 | 1009 | 74 | 2.1 |
| 26 | 37.9 | 2.37 | 37.9 | 2.37 | 46 | 59 | 1.7 |
| 27 | 38.2 | 2.36 | 38.2 | 2.36 | 387 | 40 | 1.1 |
| 28 | 39.4 | 2.28 | 39.3 | 2.29 | 799 | 44 | 1.3 |
| 29 | 39.7 | 2.27 | 39.7 | 2.27 | 921 | 56 | 1.6 |
| 30 | 40.0 | 2.25 | 40.0 | 2.26 | 713 | 48 | 1.4 |
| 31 | 45.3 | 2.000 | 45.35 | 2.00 | 533 | 41 | 1.2 |
| 32 | 45.5 | 1.995 | 44.5 | 2.04 | 434 | 39 | 1.1 |
| 33 | 46.3 | 1.96 | 46.3 | 1.96 | 929 | 48 | 1.4 |
| 34 | 46.6 | 1.95 | 46.55 | 1.95 | 327 | 40 | 1.4 |
| 35 | 47.4 | 1.92 | 47.4 | 1.92 | 442 | 35 | 1.0 |
| 36 | 48.25 | 1.89 | 48.2 | 1.89 | 50 | 35 | 1.0 |
| 37 | 48.7 | 1.87 | 48.6 | 1.875 | 789 | 54 | 1.5 |
| 38 | 48.8 | 1.87 | 48.8 | 1.87 | 412 | 53 | 1.5 |
| 39 | 49.1 | 1.86 | 49.1 | 1.855 | 808 | 54 | 1.5 |
| 40 | 51.6 | 1.77 | 51.7 | 1.77 | 1209 | 58 | 1.6 |
| 41 | 51.9 | 1.76 | 51.9 | 1.76 | 870 | 51 | 1.5 |

(b) A portion of the solids in part (a) above was calcined at 600° C. for one (1) hour, and utilized in adsorption capacity studies using a standard McBain-Bakr gravimetric adsorption apparatus. After overnight activation at 350° C., the following data were obtained:

TABLE O

| Adsorbate | Kinetic Diameter, Å | Pressure Torr | Temp., °C. | wt. % Adsorbed |
|---|---|---|---|---|
| O$_2$ | 3.4 | 100.0 | −183 | 7.6 |
| O$_2$ | 3.46 | 705.0 | −183 | 13.9 |
| neopentane | 6.2 | 101.0 | 22.7 | 4.2 |
| neopentane | 6.2 | 74. | 22.7 | 7.0 |
| n-hexane | 4.3 | 44.6 | 22.9 | 6.2 |
| H$_2$O | 2.65 | 4.6 | 23.0 | 3.8 |
| H$_2$O | 2.65 | 23.0 | 22.7 | 24.6 |

The pore size of the calcined product is greater than 6.2 Å as shown by adsorption of neopentane, kinetic diameter of 6.2 Å. X-ray analysis of the SAPO-31/AlPO$_4$-31 composite sample used in the adsorption studies established that the x-ray diffraction pattern was essentially unchanged as a result of contact with the adsorbate species.

(c) A portion of the calcined material from part (b) above was used in a test designed to show utility as a catalyst for hydrocarbon cracking. A 2.89 gram portion was reacted with a 2 mole % n-butane in helium stream at 500° C. and about 50 cm$^3$/min (STP) flow rate for 50 minutes. The pseudo-first order rate constant k$_A$ for butane consumption was 0.3.

EXAMPLE 7

The following table compares the 1-hexene conversion (at 650° F.(343° C.) and 900° F.(482° C.), as indicated, 40 psig and 8 cm$^3$/minute flow) of the SAPO-11/AlPO$_4$-11 composite catalysts (designated "COMP.") of Example 94 against physical mixtures of SAPO-11 and AlPO$_4$-11, SAPO-11 as such, and the aforementioned equivalent of ZSM-5 as to the mole percentage of total 1-hexene conversion, double bond (D.B.) isomerization, skeletal isomerization, cracking, oligomerization and other conversions:

TABLE P

| Cat. Type | COMP 2 Hrs. | COMP 4 Hrs. | COMP 6 Hrs. | COMP 24 Hrs. | PHYS MIX (30/70) | PHYS MIX (10/90) | SAPO-11 | SAPO-11 @ 900° F. | COMP 4 HRS. @ 900° F. | ZSM-5 type |
|---|---|---|---|---|---|---|---|---|---|---|
| Total Conv. | 88.50 | 92.35 | 87.95 | 91.67 | 88.56 | 87.00 | 89.10 | 95.96 | 94.64 | 96.57 |
| D. B. Isom. | 15.2 | 11.9 | 13.29 | 11.24 | 63.6 | 61.91 | 45.01 | 7.85 | 4.55 | 2.5 |
| Skel. Isom. | 66.94 | 60.68 | 64.08 | 61.52 | 30.78 | 34.85 | 44.51 | 24.86 | 17.55 | 13.22 |
| Cracking | 7.32 | 12.24 | 11.18 | 12.8 | 0.96 | 0.76 | 3.08 | 40.18 | 33.06 | 28.79 |
| Oligomer | 6.58 | 15.74 | 7.61 | 11.37 | 3.21 | 0.87 | 3.55 | 19.82 | 41.02 | 50.58 |

TABLE P-continued

| Cat. Type | COMP 2 Hrs. | COMP 4 Hrs. | COMP 6 Hrs. | COMP 24 Hrs. | PHYS MIX (30/70) | PHYS MIX (10/90) | SAPO-11 | SAPO-11 @ 900° F. | COMP 4 HRS. @ 900° F. | ZSM-5 type |
|---|---|---|---|---|---|---|---|---|---|---|
| Others | 3.96 | 0.00 | 3.83 | 3.03 | 1.46 | 1.61 | 3.85 | 7.36 | 3.83 | 4.91 |

The above table demonstrates that this composite catalyst provides a superiority over SAPO-11 per se and a blend of NZMS-11 corresponding to the phases in higher total conversion, skeletal isomerization, cracking, and oligomerization.

geneous pressure for 121.5 hours with stirring. The solids were recovered by centrifugation, washed with water, filtered, and dried in air at room temperature. A portion of the solids was subjected to x-ray and chemical analysis. The x-ray powder diffraction pattern follows:

TABLE Q

X-Ray Powder Diffraction Pattern

| PEAK % | BY HEIGHT | | BY AREA | | PEAK AREA | PEAK HEIGHT | REL. INT. |
|---|---|---|---|---|---|---|---|
| | ANGLE 2-theta | d-spacing | ANGLE 2-theta | d-spacing | | | |
| 1 | 9.44 | 9.365 | 9.4 | 9.41 | 59569 | 6080 | 100.0 |
| 2 | 12.8 | 6.89 | 12.8 | 6.92 | 4016 | 368 | 6.1 |
| 3 | 13.9 | 6.39 | 13.8 | 6.40 | 2777 | 246 | 4.1 |
| 4 | 15.95 | 5.555 | 15.9 | 5.57 | 8615 | 805 | 13.2 |
| 5 | 17.6 | 5.05 | 17.5 | 5.06 | 3598 | 282 | 4.7 |
| 6 | 19.0 | 4.68 | 18.9 | 4.69 | 1575 | 172 | 2.8 |
| 7 | 20.6 | 4.32 | 20.5 | 4.33 | 23728 | 2263 | 37.2 |
| 8 | 21.8 | 4.07 | 21.8 | 4.08 | 2941 | 254 | 4.2 |
| 9 | 22.4 | 3.98 | 22.3 | 3.98 | 878 | 77 | 1.3 |
| 10 | 23.0 | 3.87 | 22.9 | 3.88 | 2367 | 227 | 3.7 |
| 11 | 24.7 | 3.605 | 24.65 | 3.61 | 10119 | 718 | 11.8 |
| 12 | 25.9 | 3.44 | 25.85 | 3.45 | 4615 | 444 | 7.3 |
| 13 | 27.6 | 3.23 | 27.6 | 3.23 | 2149 | 182 | 3.0 |
| 14 | 27.9 | 3.19 | 27.9 | 3.195 | 1090 | 101 | 1.7 |
| 15 | 29.5 | 3.03 | 29.45 | 3.03 | 1652 | 136 | 2.2 |
| 16 | 30.6 | 2.93 | 30.5 | 2.93 | 12072 | 922 | 15.2 |
| 17 | 30.85 | 2.90 | 30.9 | 2.90 | 5273 | 43 | 7.1 |
| 18 | 31.5 | 2.84 | 31.4 | 2.85 | 915 | 75 | 1.2 |
| 19 | 33.2 | 2.695 | 33.2 | 2.70 | 1427 | 109 | 1.8 |
| 20 | 34.5 | 2.603 | 34.4 | 2.60 | 1850 | 161 | 2.7 |
| 21 | 34.9 | 2.571 | 34.9 | 2.57 | 526 | 47 | 0.8 |
| 22 | 35.7 | 2.51 | 35.7 | 2.51 | 2017 | 121 | 2.0 |
| 23 | 38.5 | 2.34 | 38.4 | 2.34 | 1291 | 81 | 1.3 |
| 24 | 39.6 | 2.27 | 39.7 | 2.27 | 1249 | 67 | 1.1 |
| 25 | 42.5 | 2.13 | 42.5 | 2.13 | 1504 | 88 | 1.4 |
| 26 | 43.3 | 2.09 | 43.3 | 2.09 | 749 | 44 | 0.7 |
| 27 | 47.6 | 1.91 | 47.6 | 1.91 | 1210 | 72 | 1.2 |
| 28 | 48.6 | 1.87 | 48.6 | 1.87 | 3955 | 227 | 3.7 |
| 29 | 50.4 | 1.81 | 50.4 | 1.81 | 3513 | 175 | 2.9 |
| 30 | 52.5 | 1.74 | 52.6 | 1.74 | 926 | 33 | 0.6 |
| 31 | 53.25 | 1.72 | 53.2 | 1.72 | 1395 | 88 | 1.5 |
| 32 | 54.1 | 1.70 | 54.1 | 1.70 | 985 | 54 | 0.9 |

EXAMPLE 8

This example demonstrates the formation of a SAPO-47 outer layer on a CoAPSO-47 deposition substrate by differential crystallization.

(a) An initial reaction mixture was prepared by dissolving 12.5 grams of cobalt acetate tetrahydrate $(Co(CH_3CO_2)_2 \cdot 4H_2O)$ in 128.5 grams of water, to which was added 112.8 grams of aluminum isopropoxide $(Al(OC_3H_7)_3)$. To the resulting mixture, 36.1 grams of an aqueous silica sol (Ludox™ LS, 30.1 wt. % $SiO_2$) was added, followed by the addition of a premixed solution of 69.3 grams of 85% orthophosphoric acid $(H_3PO_4)$, 128.7 grams of water and 71.2 grams of diethylethanolamine $[(CH_3CH_2)_2NCH_2CH_2O\,H]$. The resultant mixture had a composition in terms of molar oxide ratios of:

2.0Et$_2$NEtOH: 0.167 CoO: 0.917 Al$_2$O$_3$: 1.0 P$_2$O$_5$: 0.6 SiO$_2$: 0.6 SiO$_2$: 0.33 CH$_3$COOH: 5.5 iPrOH: 55 H$_2$O

The reaction mixture was placed in a 0.6 liter stainless steel pressure reaction vessel and heated from room temperature to 150° C. over one hour with stirring. The reaction mixture was digested at 150° C. under auto- (b) The chemical composition by bulk analysis was found to be 26.4 wt. % $Al_2O_3$, 38.6 wt. % $P_2O_5$, 5.0 wt. % CoO, 5.5 wt. % $SiO_2$, 10.6 wt. % C, 2.1 wt. % N, and 23.2 wt. % LOI. A portion of the sample was examined by conventional SEM (scanning electron microscope) survey with EDAX (energy dispersive analysis by x-ray) as well as a mounted and microtomed section. EDAX studies on clean crystals with a crystal morphology characteristic of the 47 structure-type gave the following analyses based on relative peak heights:

TABLE R

| Crystal Size (microns) | Spot Location | Co | Si | (Co + Si) |
|---|---|---|---|---|
| 30 | Center | .087 | .029 | .116 |
| | to | .099 | .029 | .128 |
| | | .021 | .113 | .134 |
| | Edge | .016 | .098 | .114 |
| 20 | Center | .073 | .057 | .130 |
| | to | .064 | .072 | .136 |
| | Edge | .057 | .078 | .135 |
| 15 | Center | .116 | .026 | .142 |
| | Edge | .035 | .095 | .130 |

TABLE R-continued

| Crystal Size (microns) | Spot Location | Co | Si | (Co + Si) |
|---|---|---|---|---|
| 10 | Center | .084 | .039 | .123 |

All but the smallest of the crystals analyzed show Co-rich centers and Si-rich peripheries.

(c) A portion of the sample was analyzed for particle size by sedigraph. Two samples were prepared using the same gel composition and differed only in reaction time. Sedigraph results revealed a noticeable increase in the average particle size when the crystallization time was increased, consistent with the observation of epitaxial growth and Co concentration gradients under the optical microscope and other related data.

(d) A portion of the solids in part (a) above was calcined at 500° C., and utilized in adsorption capacity studies using a standard McBain-Bakr gravimetric adsorption apparatus. After overnight activation at 350° C., the following data were obtained:

TABLE S

| Adsorbate | Kinetic Diameter, Å | Pressure Torr | Temp., °C. | wt. % Adsorbed |
|---|---|---|---|---|
| $O_2$ | 3.46 | 100.0 | −183 | 25.7 |
| $O_2$ | 3.46 | 700.0 | −183 | 31.3 |
| n-butane | 4.3 | 100.0 | (22-24° C.) | 8.1 |
| n-butane | 4.3 | 700.0 | (22-24° C.) | 8.6 |
| n-hexane | 4.3 | 53.0 | (22-24° C.) | 4.3 |
| $H_2O$ | 2.65 | 4.6 | (22-24° C.) | 29.4 |

(e) A portion of the calcined material from (d) above was used in a test designed to show utility as a catalyst for hydrocarbon cracking. A 2.17 gram portion was reacted with a 2 mole % n-butane in helium stream at 500° C. and about 50 cm³/min. (STP) flow rate for 50 minutes. The pseudo-first-order rate constant $k_A$ for butane Consumption Was 17.2. A 2.55 gram portion of the as synthesized sample from part (a) above was activated in situ in helium at 500° C. for 2 hours then reacted with a 2 mole % n-butane in helium stream at 500° C. and about 50 cm³/min. (STP) flow rate for 50 minutes. The pseudo-first-order rate constant $k_A$ for butane consumption was 2.4.

EXAMPLE 9

This example demonstrates the manufacture of a CoAPSO-47/SAPO-47 composite in which SAPO-47 is the deposition substrate.

(a) An initial reaction mixture was prepared by combining 80.8 grams of 85% orthophosphoric acid ($H_3PO_4$), 267.2 grams of water, and 61.5 grams of methylbutylamine (MeBuNH). To the resulting mixture, 14.4 grams of $SiO_2$ (Hi-Sil) was added followed by 51.7 grams of a hydrated pseudo-boehmite alumina (70.6 wt % $Al_2O_3$). The resultant final mixture had a composition in terms of molar oxide ratios of:

2.0 MeBuNH: 0.6 $SiO_2$: 1.0 $Al_2O_3$: 1.0 $P_2O_5$: 50 $H_2O$

The reaction mixture was placed in a 0.6 liter stainless steel pressure vessel and heated from room temperature to 200° C. over one hour with stirring. The reaction mixture was digested at 200° C. with stirring for 20 hours. At this point the reaction mixture was cooled to 50° C. and a small amount of sample was removed. The solids were collected by centrifugation, washed by vacuum filtration and dried in air at room temperature.

(b) To the remaining reaction mixture a premixed solution of 13.9 grams of cobalt acetate tetrahydrate ($Co(CH_3CO_2)_2$: 4 $H_2O$) dissolved in 46.5 grams of water was added. The resultant mixture (12984-68) had a composition in terms of molar oxide ratios of:

2.0 MeBuNH: 0.6 $SiO_2$: 0.20 CoO: 1.0 $Al_2O_3$: 1.0 $P_2O_5$: 0.4 $CH_3COOH$: 60 $H_2O$.

The reaction was mixture reheated to 150° C. over one hour with stirring and digested for 45 hours at 150° C. with stirring. The small particle solids were recovered and washed by centrifugation, while the coarser fraction was recovered by settling, washed by vacuum filtration and dried in air at room temperature.

(c) A portion of the products recovered in (a) and (b) were subjected to x-ray and chemical analysis. The x-ray powder diffraction patterns are set forth in the following tables:

TABLE T

| | X-Ray Powder Diffraction Pattern | | | | | |
|---|---|---|---|---|---|---|
| | BY HEIGHT | | BY AREA | | | | |
| PEAK % | ANGLE 2-theta | d-spacing | ANGLE 2-theta | d-spacing | PEAK AREA | PEAK HEIGHT | REL. INT. |
| 1 | 9.4 | 9.38 | 9.4 | 9.44 | 37666 | 323 | 100.0 |
| 2 | 12.8 | 6.90 | 12.8 | 6.925 | 10467 | 939 | 30.1 |
| 3 | 13.85 | 6.395 | 13.8 | 6.42 | 1387 | 120 | 3.9 |
| 4 | 15.95 | 5.56 | 15.9 | 5.57 | 5623 | 535 | 17.2 |
| 5 | 17.6 | 5.05 | 17.5 | 5.06 | 3330 | 298 | 9.5 |
| 6 | 20.5 | 4.32 | 20.5 | 4.33 | 27678 | 2603 | 85.3 |
| 7 | 21.5 | 4.14 | 21.4 | 4.14 | 2076 | 150 | 4.8 |
| 8 | 21.8 | 4.07 | 21.8 | 4.08 | 2623 | 258 | 8.3 |
| 9 | 22.3 | 3.98 | 22.3 | 3.98 | 1104 | S9 | 2.9 |
| 10 | 23.0 | 3.87 | 22.9 | 3.88 | 3931 | 361 | 11.6 |
| 11 | 24.7 | 3.61 | 24.6 | 3.61 | 14379 | 1412 | 45.2 |
| 12 | 25.8 | 3.45 | 25.8 | 3.45 | 3907 | 361 | 11.6 |
| 13 | 27.6 | 3.23 | 27.6 | 3.24 | 2348 | 193 | 6.2 |
| 14 | 27.9 | 3.20 | 27.9 | 3.20 | 1807 | 166 | 5.3 |
| 15 | 29.5 | 3.03 | 29.4 | 3.035 | 1152 | 102 | 3.3 |
| 16 | 30.5 | 2.93 | 30.5 | 2.93 | 13739 | 1180 | 37.8 |
| 17 | 30.8 | 2.90 | 30.8 | 2.90 | 4040 | 434 | 13.9 |
| 18 | 31.4 | 2.85 | 31.4 | 2.8 | 946 | 89 | 2.9 |
| 19 | 32.2 | 2.78 | 32.2 | 2.78 | 409 | 44 | 1.4 |
| 20 | 33.2 | 2.70 | 33.2 | 2.70 | 1803 | 166 | 5.3 |
| 21 | 34.4 | 2.61 | 34.4 | 2.61 | 1859 | 167 | 5.4 |
| 22 | 34.8 | 2.575 | 34.8 | 2.8 | 642 | 59 | 1.9 |
| 23 | 35.7 | 2.51 | 35.7 | 2.2 | 2339 | 189 | 6.1 |
| 24 | 37.8 | 2.38 | 37.8 | 2.38 | 588 | 39 | 1.3 |

TABLE T-continued

X-Ray Powder Diffraction Pattern

| PEAK % | BY HEIGHT | | BY AREA | | PEAK AREA | PEAK HEIGHT | REL. INT. |
|---|---|---|---|---|---|---|---|
| | ANGLE 2-theta | d-spacing | ANGLE 2-theta | d-spacing | | | |
| 25 | 38.1 | 2.36 | 38.0 | 2.37 | 733 | 47 | 1.5 |
| 26 | 38.4 | 2.34 | 38.4 | 2.35 | 946 | 68 | 2.2 |
| 27 | 38.65 | 2.33 | 38.6 | 2.33 | 321 | 46 | 1.5 |
| 28 | 38.9 | 2.31 | 38.9 | 2.315 | 710 | 54 | 1.8 |
| 29 | 39.2 | 2.30 | 39.2 | 2.30 | 490 | 51 | 1.7 |
| 30 | 39.6 | 2.28 | 39.5 | 2.28 | 1205 | 92 | 3.0 |
| 31 | 42.5 | 2.13 | 42.5 | 2.13 | 1644 | 118 | 3.8 |
| 32 | 43.3 | 2.09 | 43.3 | 2.09 | 984 | 71 | 2.3 |
| 33 | 46.7 | 1.95 | 46.7 | 1.945 | 621 | 37 | 1.2 |
| 34 | 47.6 | 1.91 | 47.55 | 1.91 | 1603 | 107 | 3.4 |
| 35 | 48.7 | 1.87 | 48.6 | 1.87 | 3791 | 185 | 5.9 |
| 36 | 49.2 | 1.85 | 49.2 | 1.85 | 371 | 41 | 1.3 |
| 37 | 49.35 | 1.85 | 49.6 | 1.84 | 457 | 34 | 1.1 |
| 38 | 50.4 | 1.81 | 50.4 | 1.81 | 2690 | 162 | 5.2 |
| 39 | 52.4 | 1.7450 | 52.4 | 1.745 | 456 | 39 | 1.3 |
| 40 | 53.15 | 1.72 | 53.2 | 1.72 | 1198 | 89 | 2.9 |
| 41 | 54.0 | 1.70 | 54.5 | 1.70 | 1069 | 71 | 2.3 |
| 42 | 54.5 | 1.68 | 54.5 | 1.68 | 970 | 70 | 2.3 |

TABLE U

X-Ray Powder Diffraction Pattern

| PEAK % | BY HEIGHT | | BY AREA | | PEAK AREA | PEAK HEIGHT | REL. INT. |
|---|---|---|---|---|---|---|---|
| | ANGLE 2-theta | d-spacing | ANGLE 2-theta | d-spacing | | | |
| 1 | 9.36 | 9.45 | 9.295 | 9.515 | 29689 | 2590 | 100.0 |
| 2 | 12.8 | 6.93 | 12.7 | 6.96 | 8498 | 784 | 30.3 |
| 3 | 13.8 | 6.435 | 13.7 | 6.45 | 141 | 1451 | 4.4 |
| 4 | 15.9 | 5.58 | 15.8 | 5.60 | 441 | 387 | 1.0 |
| 5 | 17.5 | 5.07 | 17.4 | 5.09 | 2330 | 205 | 7.9 |
| 6 | 20.5 | 4.34 | 20.4 | 4.3 | 20987 | 1993 | 76.9 |
| 7 | 21.7 | 4.09 | 21.7 | 4.09 | 2471 | 215 | 8.3 |
| 8 | 22.25 | 4.00 | 22.8 | 4.00 | 44 | 41 | 1.6 |
| 9 | 22.85 | 3.89 | 22.8 | 3.90 | 2642 | 243 | 9.4 |
| 10 | 24.6 | 3.62 | 24.5 | 3.63 | 13753 | 1283 | 49.5 |
| 11 | 25.8 | 3.46 | 2.7 | 3.46 | 3250 | 294 | 11.4 |
| 12 | 27.5 | 3.245 | 27.45 | 3.25 | 124 | 129 | 5.0 |
| 13 | 27.8 | 3.205 | 27.8 | 3.21 | 1490 | 139 | 5.4 |
| 14 | 29.35 | 3.04 | 29.3 | 3.05 | 1076 | 95 | 3.7 |
| 15 | 30.4 | 2.94 | 30.4 | 2.94 | 12341 | 1018 | 39.2 |
| 16 | 30.7 | 2.91 | 30.7 | 2.91 | 9434 | 424 | 16.4 |
| 17 | 31.3 | 2.86 | 31.3 | 2.86 | 814 | 60 | 2.3 |
| 18 | 32.1 | 2.785 | 3.1 | 2.79 | 35 | 46 | 1.8 |
| 19 | 33.1 | 2.71 | 33.0 | 2.71 | 2036 | 176 | 6.8 |
| 20 | 34.3 | 2.61 | 34.3 | 2.615 | 1936 | 148 | 5.7 |
| 21 | 35.6 | 2.52 | 3.6 | 2.52 | 1797 | 140 | 5.4 |
| 22 | 38.3 | 2.38 | 38.3 | 2.3 | 699 | 37 | 1.5 |
| 23 | 39.5 | 2.28 | 39.5 | 2.28 | 1194 | 73 | 2.8 |
| 24 | 42.35 | 2.13 | 42.3 | 2.13 | 1622 | 86 | 3.4 |
| 25 | 47.5 | 1.915 | 47.45 | 1.92 | 1234 | 75 | 2.9 |
| 26 | 48.45 | 1.88 | 48.5 | 1.88 | 2793 | 155 | 6.0 |
| 27 | 50.3 | 1.815 | 50.2 | 1.82 | 2423 | 119 | 4.6 |
| 28 | 52.3 | 1.75 | 52.3 | 1.75 | 793 | 38 | 1.5 |
| 29 | 53.0 | 1.73 | 53.0 | 1.73 | 1059 | 65 | 2.5 |
| 30 | 53.8 | 1.70 | 53.8 | 1.70 | 903 | 54 | 2.1 |
| 31 | 54.4 | 1.69 | 54.4 | 1.69 | 852 | 48 | 1.9 |
| 32 | 55.7 | 1.65 | 55.6 | 1.65 | 513 | 57 | 2.2 |
| 33 | 55.8 | 1.65 | 55.8 | 1.65 | 909 | 74 | 2.9 |

(d) The SAPO-47 portion of the sample had a chemical composition by bulk analysis of 36.6 wt. % $Al_2O_3$, 27.5 wt. % $P_2O_5$, 14.1 wt. % $SiO_2$, 8.7 wt. C, 2.0 wt. % N, 20.6 wt. % LOI. The CoAPSO-47 on SAPO-47 portion had a chemical composition by bulk analysis of 28.3 wt. % $Al_2O_3$, 35.3 wt. % $P_2O_5$, 9.0 wt. % $SiO_2$, 4.9 wt. % CoO, 11.0 wt. % C and 21.0 % wt. % LOI.

(e) Sedigraph particle size measurements were obtained on the SAPO-47 before and CoAPSO-47 after crystallization of the CoAPSO-47 layer. The results indicate an increase in the average particle size consistent with epitaxial growth.

(f) A portion of the solids in part (a) above was calcined at 500° C. and utilized in a test designed to show utility as a catalyst for hydrocarbon cracking. A 1.64 gram portion was reacted with a 2 mole % n-butane in helium stream at 500° C. and about 50 cm³/min. (STP) flow rate for 50 minutes. The pseudo-first-order rate constant $k_A$ for butane consumption was 1.6. A portion of the solids in part (b) above was calcined at 500° C. and utilized in a test designed to show utility as a catalyst for hydrocarbon cracking. A 2.30 gram portion was reacted with a 2 mole % n-butane in helium stream at 500° C. and about 50 cm³/min. (STP) flow rate for 50 minutes. The pseudo-first-order rate constant $k_A$ for butane consumption was 42.9.

EXAMPLE 10

The following is a preparation of CoAPO-31.

(a) An initial mixture was prepared by combining 230.6 grams of 85% orthophosphoric acid ($H_3PO_4$) and 593.0 grams of distilled water, to which was added 146.7 grams of a hydrated aluminum oxide (70.6 wt. % $Al_2O_3$, 29.6 wt. % LOI, pseudo-boehmite). To the resulting mixture 152.0 grams of di-n-propylamine was added, followed by the addition of 5 wt. % (dry oxide basis) of $AlPO_4$-31 seed. The resulting mixture was then divided into several portions. A solution, prepared by dissolving 10.0 grams of cobalt acetate tetrahydrate $(Co(CH_3CO_2)_2)_4.4H_2O$ in 66.9 grams of distilled water, was added to 152.4 grams of the above described mixture to form the final reaction mixture having a composition in terms of molar oxide ratios of:

1.5 $(C_6H_{15}N)$: 0.2 CoO: 1.0 $Al_2O_3$: 1.0 $P_2O_5$: 0.4 $CH_3COOH$: 58.5 $H_2O$.

The reaction mixture was placed in a sealed Teflon TM -lined stainless steel pressure vessel and heated in a oven at 150° C. under autogeneous pressure for 168 hours. The solids were recovered by centrifugation, washed with water, filtered, and dried in air at room temperature. A portion of the solids was subjected to X-ray and chemical analysis.

The product was a mixture but the major phase exhibited an x-ray powder diffraction pattern characterized by the following data:

TABLE V

| 2-Theta | d Spacing | 100 $I/I_o$ |
| --- | --- | --- |
| 8.55 | 10.3 | 74 |
| 17.1 | 5.19 | 5 |
| 20.3 | 4.37 | 18 |
| 22.1 | 4.03 | 15 |
| 22.6 | 3.93 | 100 |
| 23.2 | 3.83 | 5 |
| 25.2 | 3.53 | 4 |
| 25.4 | 3.51 | 3 |
| 25.7 | 3.46 | 5 |
| 28.0 | 3.19 | 8 |
| 29.6 | 3.02 | 4 |
| 29.8 | 3.00 | 8 |
| 31.8 | 2.82 | 12 |
| 35.2 | 2.55 | 6 |

The chemical composition was found to be 28.4 wt. $Al_2O_3$, 32.9 wt. % $P_2O_5$, 6.1 wt. % CoO, 4.4 wt. % C, 0.74 wt. % N, and 31.8 wt. % LOI. Expressed in terms of molar oxide ratios (anhydrous basis), the composition was: 0.26 $C_6H_{15}N$: 0.37 CoO: 1.20 $Al_2O_3$: 1.00 $P_2O_5$ which corresponds to an empirical chemical composition of:

0.36 $C_6H_{15}N$: $(Co_{0.08}Al_{0.50}P_{0.42})O_2$

EXAMPLE 11

The following is a preparation of CoAPSO-41:

To 18.0 grams of aluminum isopropoxide in a Waring blender was added a solution of 10.5 grams of 85 wt. % orthophosphoric acid ($H_3PO_4$) in 29.1 grams $H_2O$. This mixture was blended until it thickened and became homogeneous. To this mixture was added, in order, (1) 6.2 grams of Ludox TM LS (a colloidal silica, 30 wt.% in $H_2O$, sold by Du Pont), (2) 2.5 grams cobalt acetate $(Co(OAc)_2.4H_2O)$ dissolved in 10.1 grams $H_2O$, and (3) 10.1 grams di-n-propylamine (n-Pr2NH), each addition followed by blending the mixture until homogeneous. Finally 1.8 grams of a crystalline $AlPO_4$-41 seed was added and mixed in. The reaction mixture had a composition (without seed), expressed in molar oxide ratios of:

2.0 nPr2NH: 0.2 CoO: 0.6 $SiO_2$: 0.9 $Al_2O_3$: 0.9 $P_2O_5$: 50 $H_2O$: 0.4 HOAc: 5.4 iPrOH

The final mixture was placed in a stainless steel pressure vessel lined with polytetrafluoroethylene and heated at autogeneous pressure for 24 hours at 200° C. The crystallized product was recovered by filtration and washed, and then dried at 100 ° C. The product was a mixture but the major product exhibited an X-ray powder diffraction pattern characterized by the following data:

TABLE X

| 2 theta | d (A) | Rel. Int. |
| --- | --- | --- |
| 6.80 | 12.99 | 27 |
| 9.9 | 9.3 | 29 |
| 13.69 | 6.47 | 25 |
| 18.26 | 4.86 | 16 |
| 20.62 | 4.31 | 7 |
| 21.12 | 4.21 | 100 |
| 22.20 | 4.00 | 84 |
| 22.88 | 3.89 | 40 |
| 23.16 | 3.84 | 34 |
| 25.28 | 3.52 | 14 |
| 25.79 | 3.45 | 23 |
| 29.0 | 3.03 | 20 |
| 31.39 | 2.850 | 8 |
| 37.75 | 3.383 | 13 |
| 43.07 | 2.100 | 5 |

EXAMPLE 12

This example shows the preparation of $AlPO_4$-34.

(a) A reaction mixture was prepared by combining 51.8 grams of 85 wt. % orthophosphoric acid ($H_3PO_4$) and 130.8 grams of aqueous monoaluminum phosphate $(Al(H_2PO_4)_3$, 7.8 wt. % $Al_2O_3$, 32.8 wt. % $P_2O_5$), to which was added 368 grams of 39.3 wt. % aqueous tetraethylammonium hydroxide (TEAOH) and stirred until homogeneous. The composition of the final reaction mixture, in terms of molar oxide ratios was:

10.0 TEAOH.$Al_2O_3$.5.3 $P_2O_5$ .177 $H_2O$.

A portion of the reaction mixture (274.6 grams) was sealed in a teflon jar and was heated in an at oven 100° C. for 144 hours. The liquid- was decanted and the remaining solids were washed with $H_2O$ and dried in ambient air. The 4.6 grams of solid obtained were analyzed by x-ray powder diffraction and found to be $AlPO_4$-18, as described in Example 46 of U.S. Pat. No. 4,310,440. The decanted liquid was sealed in a Teflon TM jar and heated in an oven at 100° C. for 269 hours. 5.0 grams of calcined $AlPO_4$-5 was added to the hot reaction mixture, mixed until homogeneous, and heated at 100° C. for 71 hours. The $AlPO_4$-34 product was recovered by centrifugation, washed with $H_2O$ and dried in air at ambient temperature.

The calcined $AlPO_4$-5 employed above was prepared in a manner similar to that disclosed in Examples 1–26 of U.S. Pat. No. 4,310,440 using 85% orthophosphoric acid, hydrated alumina (pseudo-boehmite phase), and tetraethylammonium hydroxide and tripropylamine as templates. Crystallization was effected in a stirred stainless steel autoclave at 150° C. and autogeneous pressure. X-ray powder diffraction of the dried product revealed AlPO₄-5 as the sole product. The as-synthesized AlPO₄-5 was calcined in air at 600° C. for 2.5 hours then was rehydrated at ambient conditions.

A portion of the 4.6 grams of dried AlPO₄-34 product was analyzed and the following chemical analysis obtained:

TABLE Y

|  | Weight Percent |
|---|---|
| Carbon | 10.8 |
| Nitrogen | 1.4 |
| $Al_2O_3$ | 28.5 |
| $P_2O_5$ | 46.7 |
| LOI* | 25.5 |

*LOI Loss On Ignition.

The above chemical analysis corresponds to a product composition in molar oxide ratios of:

0.40 TEAOH: $Al_2O_3$: 118 $P_2O_5$: 177 $H_2O$ which corresponds to an empirical chemical composition (anhydrous basis) of:

0.092 TEAOH: $(Al_{0.46}P_{0.54})O_2$.

The x-ray powder diffraction pattern of the AlPO₄-34 product was characterized by the data in the following table:

TABLE Z

| 2-Theta | dÅ | 100 (I/I₀) |
|---|---|---|
| 9.6 | 9.24 | 100 |
| 13.0 | 6.80 | 12 |
| 14.1 | 6.27 | 11 |
| 15.6 | 5.69 | 7 |
| 16.2 | 5.48 | 23 |
| 16.8 | 5.27 | 3 |
| 17.9 | 4.94 | 14 |
| 19.1 | 4.64 | 3 |
| 20.9 | 4.25 | 41 |
| 22.1 | 4.02 | 4 |
| 22.6 | 3.94 | 3 |
| 23.3 | 3.81 | 3 |
| 25.1 | 3.54 | 15 |
| 26.3 | 3.39 | 9 |
| 28.3 | 3.16 | 3 |
| 28.3 | 3.16 | 3 |
| 30.2 | 2.959 | 4 |
| 30.9 | 2.896 | 22 |
| 32.5 | 2.73 | 3 |
| 33.9 | 2.647 | 3 |
| 34.9 | 2.570 | 3 |
| 36.5 | 2.465 | 2 |
| 39.9 | 2.258 | 2 |
| 43.3 | 2.090 | 2 |
| 49.5 | 1.842 | 2 |
| 1.3 | 1.782 | 3 |

(b) A portion of the AlPO₄-34 product obtained in part (a) was calcined in air by heating to 600° C. at 31° C./hour and holding at 600° C. for 4.5 hours. After cooling to room temperature and rehydrating in ambient air, the calcined solid had an x-ray powder diffraction pattern characterized by the data in the following table:

TABLE AA

| 2-Theta | dÅ | 100 (I/I₂) |
|---|---|---|
| 9.7 | 9.10 | 100 |
| 10.2 | 8.6 | 34 |
| 12.1 | 7.30 | 3 |
| 12.9 | 6.88 | 19 |
| 15.5 | 5.73 | 4 |
| 17.2 | 5.15 | 4 |
| 19.5 | 4.55 | 29 |
| 19.8 | 4.48 | 26 |
| 20.7 | 4.30 | 23 |
| 21.5 | 4.13 | 5 |
| 22.8 | 3.91 | 7 |
| 24.4 | 3.65 | 4 |
| 24.9 | 3.8 | 7 |
| 25.9 | 3.44 | 5 |
| 27.0 | 3.30 | 5 |
| 27.4 | 3.25 | 3 |
| 28.2 | 3.17 | 8 |
| 29.3 | 3.05 | 17 |
| 31.0 | 2.883 | 15 |
| 32.0 | 2.799 | 10 |
| 33.0 | 2.714 | 7 |
| 38.4 | 2.347 | 3 |
| 40.1 | 2.250 | 3 |
| 43.1 | 2.097 | 2 |
| 49.6 | 1.838 | 3 |
| 53. | 1.726 | 3 |

A portion of calcined AlPO₄-34 was placed in a standard McBain-Bakr gravimetric adsorption apparatus and activated under vacuum at 350° C. overnight. Subsequent adsorption data were measured as listed below. Vacuum activations at 350° C. were performed between all adsorbate changes.

TABLE BB

| Adsorbate Molecule | Kinetic Diameter, (Å) | Pressure (torr) | Temp. (°C.) | Wt. % Adsorbed |
|---|---|---|---|---|
| $O_2$ | 3.46 | 106 | −183 | 21.8 |
| $O_2$ | 3.46 | 705 | −183 | 31.7 |
| isobutane | 5.0 | 704 | 23 | 0.9 |
| n-hexane | 4.3 | 44 | 22 | 9.7 |
| $H_2O$ | 2.65 | 4.6 | 22 | 24.9 |
| $H_2O$ | 2.65 | 19 | 23 | 37.0 |

These results show that the AlPO₄-34 product is a microporous molecular sieve with a pore size at least 4.3 but less than 5.0 Å.

I claim:

1. A process for the oligomerization of linear and/or branched chain $C_2$ to $C_{12}$ olefins which comprises contacting said olefins at effective process conditions for said oligomerization with an oligomerization catalyst comprising a small or intermediate pore NZMS, nonzeolitic molecular sieve, having a pore size within range of from about 0.4 nm to 0.8 nm, as a phase of a multiphase composite comprising different inorganic crystalline compositions as phases thereof wherein at least one phase comprises a deposition substrate upon which another phase is deposited or there are multiple phases jointly formed, in which:
(a) the different phases are contiguous and have a common crystal framework structure;
(b) one phase is a small or medium pore NZMS which contains phosphorus and aluminum atoms as part of the crystal's framework structure; and
(c) the phase comprising the deposition substrate and one of the phases jointly formed constituting the deposition substrate contains at least about 20 weight percent of the total weight of the phases making up the composite.

* * * * *